United States Patent
Kim et al.

(10) Patent No.: US 10,413,575 B2
(45) Date of Patent: Sep. 17, 2019

(54) **PHARMACEUTICAL COMPOSITION FOR PREVENTING OR TREATING INFLAMMATORY DISEASES, CONTAINING *LACTOCOCCUS CHUNGANGENSIS* AS ACTIVE INGREDIENT**

(71) Applicant: CHUNG-ANG UNIVERSITY INDUSTRY-ACADEMIC COOPERATION FOUNDATION, Seoul (KR)

(72) Inventors: Won Yong Kim, Seoul (KR); Woo Jin Choi, Gyeonggi-do (KR)

(73) Assignee: Chung-Ang University Industry-Academic Cooperation Foundation, Seoul (KR)

( * ) Notice: Subject to any disclaimer, the term of this patent is extended or adjusted under 35 U.S.C. 154(b) by 0 days.

(21) Appl. No.: 15/717,154

(22) Filed: Sep. 27, 2017

(65) Prior Publication Data

US 2018/0085409 A1 Mar. 29, 2018

Related U.S. Application Data

(63) Continuation of application No. PCT/KR2016/003081, filed on Mar. 25, 2016.

(30) Foreign Application Priority Data

Mar. 27, 2015 (KR) .................. 10-2015-0043602

(51) Int. Cl.
| | |
|---|---|
| A61K 35/744 | (2015.01) |
| A61K 35/74 | (2015.01) |
| A61Q 19/00 | (2006.01) |
| A61K 8/99 | (2017.01) |
| C12R 1/46 | (2006.01) |
| C12N 1/20 | (2006.01) |

(52) U.S. Cl.
CPC .............. *A61K 35/74* (2013.01); *A61K 8/99* (2013.01); *A61K 35/744* (2013.01); *A61Q 19/00* (2013.01); *A61Q 19/007* (2013.01); *C12N 1/20* (2013.01); *C12R 1/46* (2013.01); *Y02A 50/40* (2018.01); *Y02A 50/401* (2018.01); *Y02A 50/473* (2018.01); *Y02A 50/481* (2018.01)

(58) Field of Classification Search
None
See application file for complete search history.

(56) References Cited

U.S. PATENT DOCUMENTS

| | | | | |
|---|---|---|---|---|
| 10,092,605 | B2 * | 10/2018 | Kim | .................. A23C 9/00 |
| 2008/0305089 | A1 | 12/2008 | Bufe et al. | |
| 2013/0071367 | A1 * | 3/2013 | Bauer | .................. A61K 35/74 |
| | | | | 424/93.44 |

FOREIGN PATENT DOCUMENTS

| | | |
|---|---|---|
| KR | 100123946 B1 | 11/1997 |
| KR | 1020140020685 A | 2/2014 |

OTHER PUBLICATIONS

Swift et al. 1998 (Alcohol Hangover; Alcohol Health & Research World 22(1): 54-60). (Year: 1998).*
International Search Report issued by ISA/KR in connection with PCT/KR2016/003081 dated Sep. 13, 2016.
Cho, Sung-Lim et al., *Lactococcus Chungangensis* Sp. Nov., A Lactic Acid Bacterium Isolated from Activated Sludge Foam, International Journal of Systematic and Evolutionary Microbiology, 2008, pp. 1844-1849, vol. 58, United Kingdom.
Cho, Sung-Lim, Characterization and Antimicrobial Effects of *Lactococcus* Sp. Nov. CAU 28 Isolated from Activated Sludge Foam, Master's Thesis, 2007, pp. 1-63, Graduate School of Chungang University, Medical Division, South Korea.

* cited by examiner

*Primary Examiner* — Mary Maille Lyons
(74) *Attorney, Agent, or Firm* — Levenfeld Pearlstein, LLC

(57) ABSTRACT

The composition according to the present invention, which comprises *Lactococcus chungangensis* as an active ingredient, has excellent effects of preventing or treating inflammatory diseases, inhibiting the secretion of nitric oxide and prostaglandin $E_2$, which are major inflammatory factors, and inhibiting the secretion of β-hexosaminidase and histamine, which are major factors related to allergies, and also significantly suppressing the production of skin disease-related cytokines and chemokines. Such effects are at the same level as those of conventional skin disease therapeutic agents (tacrolimus), and thus the composition can be used as a preventive or therapeutic agent against inflammatory diseases. In addition, the composition according to the present invention exhibits an antibacterial activity against *Staphylococcus aureus*, which is a microorganism inducing a secondary infection of atopic dermatitis and the like, and thus can be used in preventing or treating a bacterial infection.

2 Claims, 13 Drawing Sheets

Specification includes a Sequence Listing.

FIG. 4A
FIG. 4B
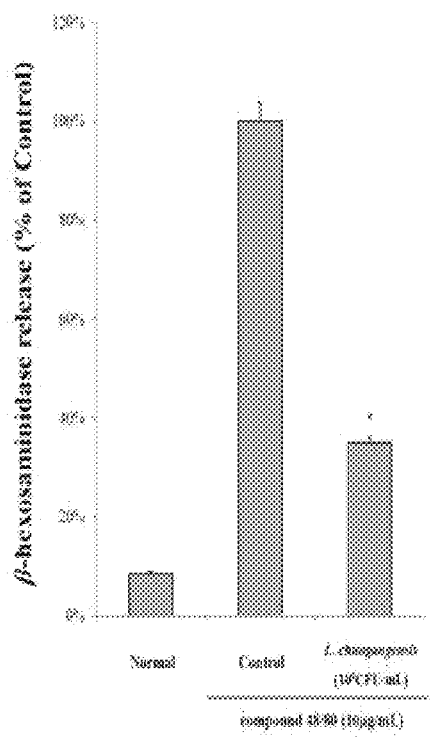
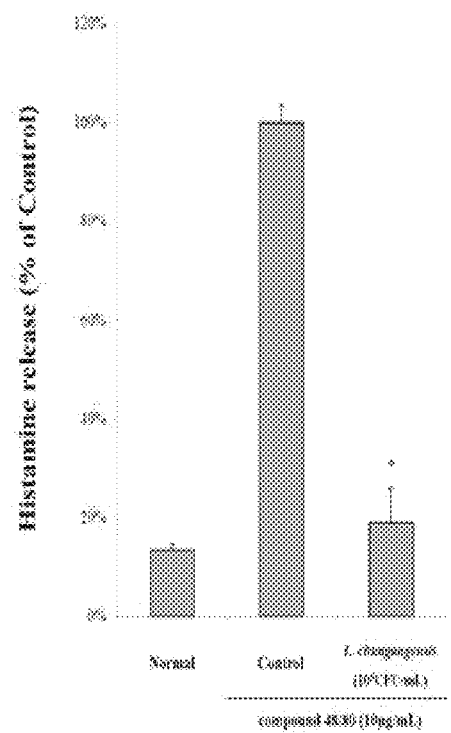

FIG. 8

|  |  | Normal | DNCB | Skin application *L. chungangensis* (10⁹CFU/mouse) | Oral administration *L. chungangensis* (10⁹CFU/mouse) | Skin application Tacrolimus (100 mg/kg) |
|---|---|---|---|---|---|---|
| BALB/c mice | Skin | | | | | |
| | Ear | | | | | |
| NC/Nga mice | Skin | | | | | |
| | Ear | | | | | |

BALB/c mice

NC/Nga mice

PHARMACEUTICAL COMPOSITION FOR PREVENTING OR TREATING INFLAMMATORY DISEASES, CONTAINING *LACTOCOCCUS CHUNGANGENSIS* AS ACTIVE INGREDIENT

CROSS-REFERENCE TO RELATED APPLICATIONS

This is a Continuation Application of International Patent Application No. PCT/KR2016/003081, filed Mar. 25, 2016, which claims the benefit of and priority to Korean Patent Application No. 10-2015-0043602, Mar. 27, 2015, the contents of which are incorporated fully by reference herein.

TECHNICAL FIELD

The present invention relates to a pharmaceutical composition comprising lactic acid bacterium *Lactococcus chungangensis* as an active ingredient for treating an inflammatory disease. Specifically, the composition according the present invention can be used in the treatment of an inflammatory disease or an allergic disease by inhibiting the release of nitric oxide and inflammatory cytokines from macrophages and suppressing the expression of histamine- or allergy-causing cytokines from mast cells. In addition, the composition according to the present invention can be used in the treatment of bacterial infection by exhibiting an antibacterial ability against *Staphylococcus aureus*, which is a microorganism causing secondary infection of atopic dermatitis and the like.

BACKGROUND ART

This application claims the priority from and the benefit of Korean Patent Application No. 10-2015-0043602 filed on Mar. 27, 2015, which is hereby incorporated in its entirety by reference as if fully set forth herein.

Inflammation is the expression of a normal and protective in vivo defense mechanism that locally occurs against tissue damages caused by physical trauma, harmful chemicals, infection by microorganisms, or irritant substances among in vivo metabolites. Such inflammation is triggered by various chemical factors produced from damaged tissues and migrating cells, while these chemical factors are known to vary according to the type of inflammation process. In normal cases, the living body neutralizes or removes pathogenic factors and regenerates damaged tissues through inflammatory responses, thereby restoring normal structures and functions, but if not, the living body may progress into a diseased state, such as chronic inflammation. In addition, in cases where inflammation is improperly triggered by harmless substances (such as pollens) or autoimmune responses (such as asthma and rheumatoid arthritis), defense responses per se damage tissues, and therefore, agents for preventing or treating inflammatory diseases are needed. Inflammatory responses can be observed in almost all clinical diseases, some of which are bacterial diseases being able to be treated by causative therapy through administration of antibiotics, while most of inflammatory diseases are known as incurable diseases having no specific treatments since such inflammatory diseases are caused by tissue damage due to autoimmune responses.

The most typical agents for preventing or treating such inflammatory diseases are largely classified into steroidal and non-steroidal agents, respectively. Among these agents, most of synthetic agents for preventing or treating inflammatory diseases have many side effects, besides their main functions. That is, in order to treat inflammatory diseases, nonsteroidal anti-inflammatory drugs (NSAIDs) are used to alleviate the inflammation; steroids are used in cases of severe inflammation or no efficacy of NSAIDs; and immunosuppressive drugs or surgery is employed in cases of intractable inflammation. Here, the NSAIDs mainly inhibit cyclooxygenase (COX) to suppress the production of prostaglandins involved in inflammatory responses, and thereby exhibiting actions of preventing or treating inflammatory diseases. However, they cause side effects (such as gastrointestinal disorders, hepatic disorders, kidney dysfunctions, and the like), and thus the long-term use of NSAIDs is difficult.

Meanwhile, allergies are systemic or local disorders of the living body based on immune responses which are the aggregation of a wide range of complex pathological phenomena. Allergies in the human body are classified into Types I, II, III, and IV according to their immune mechanisms, respectively. Among these, Type I allergies, which are involved in an immediate hypersensitivity reaction, account for an important part in the clinical practice, and include atopic dermatitis, allergic rhinitis, bronchial asthma, hay fever, and pollinosis.

It was discovered in 1953 that Type I allergies occur by the activation of mast cells, and granules of such mast cells contain a large quantity of histamine, which is a mediator of inflammatory responses. The release of histamine from mast cells in allergic responses was discovered. While the mechanisms for these phenomena were being researched, immunoglobulin E (IgE) was discovered by Ishizaka, and such discovery served as an important factor to reveal that mast cells are involved in immediate allergic responses. That is, the high-affinity IgE receptors are present on the surface of mast cells, while IgE binds to such receptors and then antigens again binds thereto, thereby forming cross-linkage, causing a degranulation reaction, so that the contents in granules, that is, synthesized and stored preformed mediators, such as histamine, serotonin, and bradykinin, and protease, proteoglycan, and the like are simultaneously released (Ishizaka, Hosp Pract.; 12(1):57-67, 1977).

Type I allergies may be summarized as a natural phenomenon of the living body, which is caused by active amines and proteases, which are granular contents released by the activation of mast cells, lipid mediators produced from cell membrane phospholipids, and cytokines, such as IL-3 (mast cell proliferation factor), IL-4, and IL-5, which are well known as modulators of immune responses (Galli S J et al., Curr Opin Immunol.; 3(6):865-872, 1991; Bradding P et al., J Immunol.; 151(7):3853-3865, 1993).

In addition, when the skin is exposed to an allergic antigen, antigen-specific IgE binds to an IgE receptor on the surface of Langerhans cells, and is transferred to T cells on the surface of the antigen, thereby activating the T cell. Unlike normal state, in allergic skin diseases, especially atopic dermatitis, Th2 is activated to release cytokines, such as IL-4, IL-5, IL-6, IL-8, IL-10 and IL-13, thereby promoting the production of IgE in B cells and promoting the degranulation of activated mast cells, so that cytokines and histamine are released (Baruah C. C. et al., Pharmacol Res.; 38(6):487-92, 1998; Karadag C. H. et al., Braz J Med Biol Res.; 33(3):327-330, 2000; Paolini R. et al., Nature.; 353 (6347):855-858, 1991).

Currently, allergy drugs that are clinically used may be broadly classified into a degranulation inhibitor, a chemical transmitter action inhibitor, a chemical transmitter synthesis inhibitor, and the like, according to their action mechanism.

Among these drugs, the chemical transmitter action inhibitor and the chemical transmitter synthesis inhibitor have a relatively clear site of drug action, whereas the degranulation inhibitor has an unclear action mechanism, and these drugs may incur several side effects due to their long-term administration. Therefore, for treatment of Type I allergies, it may be very important to elucidate action mechanisms of the production and release of these physiologically active substances in mast cells and to minimize side effects due to their long-term use.

DETAILED DESCRIPTION OF THE INVENTION

Technical Problem

The present inventors, during the research to discover a therapeutic agent with high efficacy and few side effects for treating an inflammatory disease or an allergic disease from the lactic acid bacterium *Lactococcus chungangensis*, have confirmed that *Lactococcus chungangensis* of the present invention significantly inhibits the production of cytokines and chemokines related to inflammation or allergies, has excellent effects of inhibiting the release of major inflammation factors, i.e., nitric oxide and prostaglandin $E_2$, has excellent effects of inhibiting the release of main atopic factors, i.e., β-hexosaminidase and histamine, and has a therapeutic effect at the same level as known existing medicines when applied to an atopy-induced animal model, leading to the completion of the present invention.

Therefore, an aspect of the present invention is to provide a pharmaceutical composition for treating an inflammatory disease, the composition comprising *Lactococcus chungangensis* (Accession No.: KCTC 12684BP) as an active ingredient.

Another aspect of the present invention is to provide a food composition for treating an inflammatory disease, the composition comprising *Lactococcus chungangensis* as an active ingredient.

Another aspect of the present invention is to provide a cosmetic composition for treating an inflammatory disease, the composition comprising *Lactococcus chungangensis* as an active ingredient.

Another aspect of the present invention is to provide an externally-applied dermal agent for treating an inflammatory disease, the agent comprising *Lactococcus chungangensis* as an active ingredient.

Still another aspect of the present invention is to provide a pharmaceutical composition for treating a bacterial infection, the composition comprising *Lactococcus chungangensis* as an active ingredient.

Another aspect of the present invention is to provide a food composition for treating a bacterial infection, the composition comprising *Lactococcus chungangensis* as an active ingredient.

Another aspect of the present invention is to provide a cosmetic composition for treating a bacterial infection, the composition comprising *Lactococcus chungangensis* as an active ingredient.

Another aspect of the present invention is to provide an externally-applied dermal agent for a treating bacterial infection, the agent comprising *Lactococcus chungangensis* as an active ingredient.

Still another aspect of the present invention is to provide a method for treating an inflammatory disease, the method comprising administering an effective amount of *Lactococcus chungangensis* to a subject in need thereof.

Another aspect of the present invention is to provide a use of *Lactococcus chungangensis* for preparing an agent for treating an inflammatory disease.

Still further aspect of the present invention is to provide a method for treating a bacterial infection, the method comprising administering an effective amount of *Lactococcus chungangensis* to a subject in need thereof.

Another aspect of the present invention is to provide a use of *Lactococcus chungangensis* for preparing an agent for treating a bacterial infection.

Technical Solution

In accordance with an aspect of the present invention, there is provided a pharmaceutical composition for treating an inflammatory disease, the composition comprising *Lactococcus chungangensis* (accession number: KCTC 12684BP) as an active ingredient.

In accordance with another aspect of the present invention, there is provided a food composition for treating an inflammatory disease, the composition comprising *Lactococcus chungangensis* as an active ingredient.

In accordance with another aspect of the present invention, there is provided a cosmetic composition for treating an inflammatory disease, the composition comprising *Lactococcus chungangensis* as an active ingredient.

In accordance with another aspect of the present invention, there is provided an externally-applied dermal agent for treating an inflammatory disease, the agent comprising *Lactococcus chungangensis* as an active ingredient.

In accordance with still another aspect of the present invention, there is provided a pharmaceutical composition for treating a bacterial infection, the composition comprising *Lactococcus chungangensis* as an active ingredient.

In accordance with another aspect of the present invention, there is provided a food composition for treating a bacterial infection, the composition comprising *Lactococcus chungangensis* as an active ingredient.

In accordance with another aspect of the present invention, there is provided a cosmetic composition for treating a bacterial infection, the composition comprising *Lactococcus chungangensis* as an active ingredient.

In accordance with another aspect of the present invention, there is provided an externally-applied dermal agent for treating a bacterial infection, the agent comprising *Lactococcus chungangensis* as an active ingredient.

In accordance with still another aspect of the present invention, there is provided a method for treating an inflammatory disease, the method comprising administering an effective amount of *Lactococcus chungangensis* to a subject in need thereof.

In accordance with another aspect of the present invention, there is provided a use of *Lactococcus chungangensis* for preparing an agent for treating an inflammatory disease.

In accordance with another aspect of the present invention, there is provided a method for treating a bacterial infection, the method comprising administering an effective amount of *Lactococcus chungangensis* to a subject in need thereof.

In accordance with another aspect of the present invention, there is provided a use of *Lactococcus chungangensis* for preparing an agent for treating a bacterial infection treatment.

Hereinafter, the present invention will be described in detail.

The present invention provides a pharmaceutical composition for treating an inflammatory disease, the composition comprising *Lactococcus chungangensis* as an active ingredient.

In addition, the present invention provides the composition wherein *Lactococcus chungangensis* has an accession number of KCTC 12684BP.

*Lactococcus chungangensis* according to the present invention, is a strain isolated from wastewater in a wastewater treatment plant, and belongs to a Gram-positive coccus taxonomically. The strain according to the present invention is a novel strain that was discovered by the present inventors, identified as a strain pertaining to the genus *Lactococcus* based on cytomorphological and biochemical test results, and deposited with the Korean Culture Type Collection in 2008 (Accession No.: KCTC 12684BP). In addition, *Lactococcus chungangensis* is a Gram-positive coccus, and characterized by forming no spores and mycelium and being generated in the form of a short chain or an irregular cluster alone or in pair. Specific descriptions of the strain can be found in "International Journal of Systematic and Evolutionary Microbiology (2008), 58, 18441849".

Not only the strain *Lactococcus chungangensis* but also a culture fluid or culture supernatant of the strain exhibits an effect on an inflammatory disease, and thus, the composition of the present invention encompasses, in its scope of right, a pharmaceutical composition for treating an inflammatory disease, the pharmaceutical composition comprising the strain, or a culture fluid or culture supernatant thereof. *Lactococcus chungangensis* may be removed from the culture fluid, while the culture fluid is preferably a supernatant after centrifugation. The culture fluid may include a concentrate of the culture fluid and a dried product of the culture fluid. In addition, the composition of the present invention may contain, as an active ingredient, *Lactococcus chungangensis* viable cells, crushed cell wall fractions, dead cells, or dried cells, and may further contain an excipient or a carrier.

A method for culturing *Lactococcus chungangensis* of the present invention is not particularly limited, and may be performed by general methods. For example, the strain may be cultured in a medium in which microorganisms can grow, and recovered by using a method such as centrifugation or the like.

According to an Example of the present invention, macrophages RAW264.7 were treated with *Lactococcus chungangensis* and then cultured for 24 hours. It was verified that, in the LPS-stimulated RAW264.7, the production of nitric oxide (NO) was remarkably reduced and the production of prostaglandin $E_2$ ($PGE_2$) also showed a similar pattern. Thus, it could be seen that *Lactococcus chungangensis* is effective in inhibiting an inflammatory response (Example 2-2).

In addition, according to another Example of the present invention, in a DNCB-induced atopic animal model, oral administration or skin application of *Lactococcus chungangensis* at $10^9$ cells/mouse was carried out twice per week for a total of 4 weeks. As a result, it was verified that the levels of inflammatory response-related cytokines, IL-4, IL-5, IL-12, IFN-$\gamma$, TNF-$\alpha$, and TARC in the blood were significantly decreased, and thus, it could be seen that *Lactococcus chungangensis* can be used as an agent for preventing or treating an inflammatory disease (Example 4-5).

The composition of the present invention may further contain a pharmaceutically acceptable additive. Examples of the pharmaceutically acceptable additive may include starch, gelatinized starch, microcrystalline cellulose, lactose, povidone, colloidal silicon dioxide, calcium hydrogen phosphate, lactose, mannitol, taffy, Arabic gum, pre-gelatinized starch, corn starch, cellulose powder, hydroxypropyl cellulose, Opadry, sodium carboxymethyl starch, carnauba wax, synthetic aluminum silicate, stearic acid, magnesium stearate, aluminum stearate, calcium stearate, white sugar, dextrose, sorbitol, talc, and the like. The pharmaceutically acceptable additive according to the present invention is preferably contained in 0.1-90 parts by weight relative to the pharmaceutical composition, but is not limited thereto.

In addition, the composition of the present invention may be administered in various oral or parental dosage forms at the time of actual clinical administration, and may be formulated by using a diluent or a vehicle, such as a filler, an extender, a binder, a wetting agent, a disintegrant, or a surfactant, which is generally used in formulations.

Solid preparations for oral administration may include a tablet, a pill, a powder, granules, a capsule, and the like. Such solid preparations may be prepared by mixing *Lactococcus chungangensis* with at least one vehicle, for example, starch, calcium carbonate, sucrose, lactose, gelatin, or the like. In addition to simple excipients, lubricants, such as magnesium stearate and talc, may be used. Liquid preparations for oral administration include a suspension, a liquid for internal use, oil, syrup, and the like, and may also include, in addition to simple diluents that are frequently used, such as water and liquid paraffin, various excipients, for example, a wetting agent, a sweetener, an aroma, a preservative, and the like.

Preparations for parenteral administration may include a sterile aqueous solution, a non-aqueous solvent, a suspension, an emulsion, a freeze-dried preparation, and a suppository. The non-aqueous solvent and the suspension solvent may include propylene glycol, polyethylene glycol, vegetable oil such as olive oil, an injectable ester such as ethylolate, and the like. As a substrate for the suppository, Witepsol, Macrogol, twin 61, cacao butter, laurin butter, or glycerogelatin may be used.

Meanwhile, the injection may contain conventional additives, such as a solubilizer, an isotonic agent, a suspending agent, an emulsifier, a stabilizer, and a preservative.

In addition, the therapeutic composition according to the present invention may further contain any physiologically acceptable carrier, excipient, or stabilizer (Remington: The Science and Practice of Pharmacy, 19th Edition, Alfonso, R., ed, Mack Publishing Co. (Easton, Pa.: 1995)). The acceptable carrier, excipient, or stabilizer is non-toxic to a user at the used dose and concentration, and includes: buffers such as phosphoric acid, citric acid, and other organic acids; antioxidants such as ascorbic acids; low-molecular weight (less than about 10 residues) polypeptides; proteins such as serum albumin, gelatin, or immunoglobulin; hydrophilic polymers such as polyvinyl pyrrolidone; amino acids such as glycine, glutamine, asparagine, arginine, or lysine; monosaccharides, disaccharides, and other carbohydrates such as glucose, mannose, or dextrin; chelating agents such as EDT; sugar alcohols such as mannitol or sorbitol; salt-forming counter ions such as sodium; and/or non-ionic surfactants such as Tween, pluronics, or polyethylene glycol (PEG).

The dose of the pharmaceutical composition of the present invention with respect to the human body may vary depending on patient's age, body weight, gender, the mode of administration, the state of health, and the severity of disease. The dose may be generally 0.01-100 mg/kg/day, preferably 0.1-20 mg/kg/day, and more preferably 5-10 mg/kg/day. The composition may also be divisionally administered at predetermined intervals according to the determination of a doctor or pharmacist.

The present invention provides a composition wherein the inflammatory disease is any one selected from the group consisting of inflammatory skin diseases, allergic diseases, inflammatory bowel diseases such as Crohn's disease and ulcerative colitis, peritonitis, osteomyelitis, cellulitis, meningitis, encephalitis, pancreatitis, trauma-induced shock, bronchial asthma, cystic fibrosis, stroke, acute bronchitis, chronic bronchitis, acute bronchiolitis, chronic bronchiolitis, osteoarthritis, gout, spondyloarthropathy, ankylosing spondylitis, Reiter's syndrome, psoriatic arthropathy, spondylitis associated with bowel disease, juvenile arthropathy, juvenile ankylosing spondylitis, reactive arthropathy, infectious arthritis, post-infectious arthritis, gonococcal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Lou Gehrig's granulomatosis, polymyalgia rheumatica, joint cell arteritis, calcium crystal deposition arthropathy, pseudo gout, non-articular rheumatism, bursitis, tendosynovitis, epicondylitis (tennis elbow), neuropathic joint disease (charco and joint), hemarthrosis, Henoch-Schönlein purpura, hypertrophic osteoarthropathy, multicentric reticulohistiocytoma, surcoilosis, hematochromatosis, sickle-cell disease and other hemoglobinopathies, hyperlipoproteinemia, hypogammaglobulinemia, familial Mediterranean fever, Behat's disease, systemic lupus erythematosus, relapsing fever, psoriasis, multiple sclerosis, septicemia, septic shock, multi-organ dysfunction syndrome, acute respiratory distress syndrome, chronic obstructive pulmonary disease, acute lung injury, and broncho-pulmonary dysplasia, but is not limited thereto.

The present invention provides a composition wherein the allergic disease is any one selected from the group consisting of allergic skin diseases, atopic dermatitis, bronchial asthma, allergic rhinitis, allergic conjunctivitis, allergic otitis media, rash, asthma, and anaphylactic shock, but is not limited thereto.

As used herein, the term "allergy" refers to a phenomenon in which a biological body, which is in contact with a foreign material, shows a response different from a normal response to the foreign material. An allergy is a systemic or topical disorder of the biological body based on an immune response due to the aggregation of a wide range of complex pathological phenomena. Allergies in the human body are classified into Types I, II, III, and IV according to the immune mechanism, respectively. Among these, Type I allergy, which is involved in an immediate hypersensitivity reaction, accounts for an important part of the clinical practice, and includes atopic dermatitis, allergic rhinitis, bronchial asthma, hay fever, and pollinosis.

In addition, the allergic diseases may be mediated by mast cells. Particularly, *Lactococcus chungangensis* can exhibit its effect on an allergic disease by inhibiting degranulation in mast cells.

According to an Example of the present invention, HMC-1 mast cells were treated with *Lactococcus chungangensis*, and then treated with compound 48/80 which induces degranulation in mast cells. As a result, it was verified that the release of β-hexosaminidase, which is a major factor of activation and degranulation of mast cells, was inhibited, while the release of histamine, which is one of the most important factors causing allergic diseases, was also significantly inhibited (Example 3).

In addition, according to another Example of the present invention, the expression level of IgE, which is a cytokine that mediates allergic diseases, was determined in the serum of BALB/c mice or NC/Nga mice orally administered or skin-applied with *Lactococcus chungangensis*. As a result, it was verified that *Lactococcus chungangensis* had efficacy in inhibiting IgE expression at the equivalent extent compared with positive control Tacrolimus (Example 4-4), and therefore, it could be seen that *Lactococcus chungangensis* can be favorably used for the prevention or treatment of allergic diseases.

Particularly, *Lactococcus chungangensis* according to the present invention has almost no toxicity and shows effects of preventing and treating allergic skin diseases by its anti-inflammatory and anti-allergic effects, and has excellent effects of inhibiting the allergic inflammatory responses and the expression of inflammatory cytokines and thus has an excellent effect on allergic skin diseases including atopic dermatitis, so that a pharmaceutical composition comprising *Lactococcus chungangensis* can be used in the prevention and treatment of allergic skin diseases.

It is known that atopic dermatitis starts with infantile eczema called congenital fever. In its acute phase, the skin is itchy, redden, swollen, wet, or scabbed, or has millet-like bumps or small blisters. In its chronic phase, the skin is itchy, calloused, thickened, darkened, or bleached white, or has lines or rice flour-like scales.

The findings of the blood test and skin biopsy of atopic dermatitis patients generally show that IgE Receptor I expression and eosinophils as well as IgE and monocytes are increased in the blood, while IgE receptor-expressed antigen-presenting cells, activated T cells, IL-5, IL-10, IL-13, and eosinophils are increased in the skin. Atopic dermatitis patients show an increase of immunological adverse events, that is, immediate hypersensitivity reactions to environmental antigens, an increase in the expression of IgE and IgE receptor, and an increase of antigen-specific T cells and Th2 cells. Patients with chronic atopic dermatitis show a binary cytokine profile in which Th1 cells are increased. In addition, the activation of Langerhans cells and memory T cells, the increase of dendritic cells and eosinophils, and the activation of mast cells occur in the epidermis.

According to an Example of the present invention, in BALB/c mouse and NC/Nga mouse animal models with atopic dermatitis induced by DNCB, the therapeutic effects in *Lactococcus chungangensis* oral administration group, *Lactococcus chungangensis* skin application group, and a Tacrolimus skin application group as a positive control were observed. As a result, it was verified that the formation of dead cells, erythema, and exudative crusts, and symptoms, such as bleeding and swelling, which are skin pathological states observed by the naked eye, were remarkably improved in the *Lactococcus chungangensis* oral administration group and the Tacrolimus skin application group, and the skin conditions were generally improved in the *Lactococcus chungangensis* skin application group. In addition, it was also verified that in the evaluation of the number of scratching events in mice, the scratching events in the *Lactococcus* oral administration group were remarkably reduced at the same level as in the Tacrolimus treatment group (Example 4-2).

In addition, in another Example of the present invention, the effects of *Lactococcus chungangensis* on the expression of chemokine and cytokine genes related to atopic dermatitis were evaluated in the skin tissues of atopic dermatitis animal models. As a result, it was verified that the mRNA expression levels of IL-4, IL-5, IL-12, IFN-γ, TNF-α, and TARC in the skin tissues were reduced in the *Lactococcus chungangensis* oral administration group and the Tacrolimus skin application group as a positive control (Example 4-5), while the expression levels of the chemokine and cytokine proteins were significantly reduced in blood samples taken from hearts (Example 4-5). Therefore, it could be seen that the *Lactococcus chungangensis* of the present invention may be effective at a similar level to Tacrolimus which is used as an atopic dermatitis medicine, and thus, can be used as an agent for preventing or treating allergic skin diseases including atopic dermatitis.

The present invention also provides a food composition for treating an inflammatory disease, the composition comprising *Lactococcus chungangensis* as an active ingredient.

The inflammatory disease is as described above.

In the food composition of the present invention, *Lactococcus chungangensis* may be added per se or may be used together with other foods or food ingredients, and may be properly used by a conventional method.

As used herein, the term "food" includes meat, sausage, bread, chocolate, candies, snacks, cookies, pizza, ramen, other noodles, gums, dairy products including ice cream, various soups, beverages, teas, drinks, alcoholic beverages, vitamin complexes, and the like, and encompasses all types of foods in an acceptable meaning.

The food composition of the present invention may include a health functional food. As used herein, the term "health functional food" refers to a food that is manufactured and processed in the form of a tablet, a capsule, a powder, granules, a liquid, and a pill by using functional raw materials or ingredients beneficial for the human body. Here, the term "functional" refers to obtaining beneficial effects for a health purpose, such as nutrient control or physiological actions, with respect to a structure and function of the human body. The health functional food according to the present invention may be manufactured by a method that is commonly used in the art, while being manufactured by adding raw materials and ingredients that are conventionally added in the art.

In addition, any dosage form of the health functional food may also be prepared without limitation as long as the dosage form is acceptable as health functional food. The food composition of the present invention may be prepared in various dosage forms. The food composition of the present invention uses a food as a raw material unlike general medicines, so that the food composition has no side effects that may occur due to the long-term use of a medicine, and has excellent portability, and therefore, the health functional food of the present invention can be taken as a supplement for enhancing the effects of anti-inflammatory or anti-allergic agents.

In addition, the food composition of the present invention may contain various nutrients, vitamins, electrolytes, flavorants, colorants, pectic acid and salts thereof, alginic acid and salts thereof, organic acids, protective colloid thickeners, pH adjusters, stabilizers, stabilizing agents, preservatives, glycerins, alcohols, carbonating agents used in carbonated drinks, and the like. In addition, the food composition of the present invention may contain pulps for manufacturing natural fruit juice, fruit juice drink, and vegetable drink. These ingredients may be used independently or in combination. Although the proportion of such an additive is not greatly important, the additive may be generally selected within a range of 0.01-0.1 parts by weight relative to 100 parts by weight of the food composition of the present invention, but is not limited thereto.

In addition, the food composition of the present invention may contain various flavorants or natural carbohydrates as additional ingredients, like in ordinary beverages. The carbohydrates are monosaccharides, such as glucose and fructose, disaccharides such as maltose and sucrose, and polysaccharides such as dextrin and cyclodextrin, and sugar alcohols, such as xylitol, sorbitol, and erythritol. Natural sweetening agents, such as thaumatin and *stevia* extracts, and synthetic sweetening agents, such as saccharin and aspartame, may be used as a sweetening agent. The proportion of the natural carbohydrates may be generally about 0.01-0.04 g, and preferably about 0.02-0.03 g per 100 mL of the composition of the present invention, but is not limited thereto.

The mixing amount of *Lactococcus chungangensis* in the food composition of the present invention may be appropriately determined according to its respective use (prevention, health, or therapeutic treatment).

In general, *Lactococcus chungangensis* of the present invention is added in an amount of $1 \times 10^7$ to $1 \times 10^9$ (microbial count), and preferably $1 \times 10^8$ to $5 \times 10^8$, relative to 1 g (or ml) of a specific food material in the manufacture of a food or beverage. In addition, the daily intake of *Lactococcus chungangensis* food composition of the present invention is $1 \times 10^5$ to $1 \times 10^{10}$ CFU/kg, and preferably $1 \times 10^5$ to $1 \times 10^7$ CFU/kg. The intake may be once a day or may be divided into several portions, but is not limited thereto.

The effective dosage of the strain of the present invention may be used in corresponding to the effective dosage of the pharmaceutical composition, but may be less than the above range for long-term intake for the purpose of health and hygiene or health control. Since the active ingredient has no problem in view of safety, the effective dosage of the strain of the present invention may exceed the above described range.

The present invention also provides a cosmetic composition for treating an inflammatory disease, the composition comprising *Lactococcus chungangensis* as an active ingredient.

The inflammatory disease is as described above.

In the cosmetic composition according to the present invention, a dosage form as a cosmetic product including the cosmetic composition may further contain, in addition to *Lactococcus chungangensis*, an adjuvant that is commonly used in the fields of cosmetology or dermatology, such as a fatty substance, an organic solvent, a solubilizing agent, and gelling agent, a softening agent, an antioxidant, a suspending agent, a stabilizing agent, a forming agent, a flavorant, a surfactant, an ionic or nonionic emulsifier, a filler, a sequestering agent, a chelating agent, a preservative, vitamins, a blocker, a wetting agent, essential oil, a dye, a pigment, a hydrophilic or lipophilic activator, a lipid vesicle, or any other ingredient conventionally used in a cosmetic product. In addition, the above ingredients may be introduced in amounts that are generally used in cosmetology.

A specific dosage form of the composition according to the present invention as a cosmetic product includes skin lotion, skin softener, skin toner, astringent, lotion, milk lotion, moisture lotion, nourishing lotion, massage cream, nourishing cream, moisture cream, hand cream, essence, nourishing essence, pack, soap, shampoo, cleansing foam, cleansing lotion, cleansing cream, body lotion, body cleanser, milky lotion, pressed powder, loose powder, eye shadow, and the like, but is not limited thereto.

The present invention also provides an externally-applied dermal agent for treating an inflammatory disease, the agent comprising *Lactococcus chungangensis* as an active ingredient.

The inflammatory disease is as described above.

In cases where the composition of the present invention is prepared as an externally-applied dermal agent, the composition of the present invention contains not only the above described *Lactococcus chungangensis* but also ingredients normally used in the externally-applied dermal agent, for example, carriers and general additives, such as an antioxidant, a stabilizer, a solubilizer, vitamins, a pigment, and a flavorant. Further, in addition to *Lactococcus chungangensis*, the composition of the present invention may be used together with conventional skin wetting agents, skin sealants, and ceramide-containing moisturizers, as long as the functions thereof are not hindered.

The externally-applied dermal agent of the present invention may be formulated into any dosage form that is conventionally prepared, and examples thereof may include a solution, suspension, emulsion, paste, gel, cream, lotion, powder, soap, surfactant-containing cleansing, oil, powder foundation, emulsion foundation, wax foundation, and spray, but are not limited thereto. More specifically, the externally-applied dermal agent of the present invention may be prepared in the dosage form of emollient lotion, nourishing lotion, nourishing cream, massage cream, essence, eye cream, cleansing cream, cleansing foam, cleansing water, pack, spray, or powder.

In cases where the dosage form of the present invention is a paste, a cream, or a gel, animal oil, vegetable oil, wax, paraffin, starch, tragacanth, a cellulose derivative, polyethylene glycol, silicone, bentonite, silica, talc, or zinc oxide may be used as a carrier ingredient.

In cases where the dosage form of the present invention is a powder or a spray, lactose, talc, silica, aluminum hydroxide, calcium silicate, or a polyamide powder may be used as a carrier ingredient. Especially, in cases where the dosage form of the present invention is a spray, the spray may further include a propellant, such as chlorofluorohydrocarbon, propane/butane, or dimethyl ether.

In cases where the dosage form of the present invention is a solution or an emulsion, a solvent, a solubilizer, or an emulsifier may be used as a carrier ingredient, and examples thereof include water, ethanol, isopropanol, ethyl carbonate, ethyl acetate, benzyl alcohol, benzyl benzoate, propylene glycol, 1,3-butyl glycol oil, glycerol aliphatic ester, polyethylene glycol, or fatty acid ester of sorbitan.

In cases where the dosage form of the present invention is a suspension, a liquid diluent (such as water, ethanol, or propylene glycol), a suspending agent (such as ethoxylated isostearyl alcohol, polyoxyethylene sorbitol ester, or polyoxyethylene sorbitan ester), microcrystalline cellulose, aluminum metahydroxide, bentonite, agar, or tragacanth may be used as a carrier ingredient.

In cases where the dosage form of the present invention is a surfactant-containing cleansing, aliphatic alcohol sulfate, aliphatic alcohol ether sulfate, sulfosuccinate monoester, isethionate, imidazolium derivatives, methyl taurate, sarcosinate, fatty acid amide ether sulfate, alkyl amido betaine, aliphatic alcohol, fatty acid glyceride, fatty acid diethanolamide, vegetable oil, lanoline derivatives, or ethoxylated glycerol fatty acid ester may be used as a carrier ingredient.

The present invention provides a pharmaceutical composition for treating a bacterial infection, the composition comprising *Lactococcus chungangensis* as an active ingredient.

The present invention also provides a food composition for treating a bacterial infection, the composition comprising *Lactococcus chungangensis* as an active ingredient.

The present invention also provides a cosmetic composition for treating a bacterial infection, the composition comprising *Lactococcus chungangensis* as an active ingredient.

The present invention also provides an externally-applied dermal agent for treating bacterial infection, the agent comprising *Lactococcus chungangensis* as an active ingredient.

According to an Example of the present invention, it could be verified that the composition comprising comprising *Lactococcus chungangensis* as an active ingredient according to the present invention had an effect of preventing or treating a bacterial infection by exhibiting an anti-bacterial action on *Staphylococcus aureus* (Example 5).

Specific examples of the bacteria may be harmful microorganisms, such as *E. coli, Salmonella typhimurium, Staphylococcus aureus, Candida albicans, Aspergillus niger*, or *Propionibacterium acnes*, and preferably *Staphylococcus aureus*, but are not limited thereto.

Meanwhile, the bacterial infection may mean that bacteria invade through the skin of a patient having atopic dermatitis to cause infection, but is not limited thereto. Patients with atopic dermatitis have very dry and itchy skin, and thus continue scratching, resulting in skin damage. Harmful substances, such as bacteria and viruses, invade through these wounds to cause secondary infection, resulting in inflammation, and in severe cases, causing accompanying symptoms, such as chills and fever.

*Staphylococcus aureus* is the most common bacterium that causes a secondary infection caused by atopic dermatitis. It was revealed that *Staphylococcus aureus* is present in only 5% of normal persons, while skin lesions were colonized in 90% or more of patients with atopic dermatitis (Leyden, J E, Marples, R P and Kligman A M Br. J. Dermatol. 90:525-530, 1974). The bacteria seem to cause the exacerbation or chronicization of atopic dermatitis in such patients through the release of toxins (e.g., enterotoxins A, B, C, and D; toxic shock syndrome toxins), and most of the toxins are highly antigenic in nature and thus exacerbate an inflammatory response in the skin (Leung, D Y M et al J. Clin. Invest. 92 1374-80, 1993). A particular study with respect to children showed that the severity of a disease is associated with colonization by a toxin-producing strain, and verified that 81% of patients had *Staphylococcus aureus* colonization (4% in the control) (Bunikowski, R et al J. Allergy Clin Immunol. 105(4):814-819, 2000).

Therefore, it is very important that the composition according to the present invention showing an anti-bacterial activity against *Staphylococcus aureus* can improve the symptoms of atopic dermatitis and prevent or alleviate a secondary infection caused by atopic dermatitis.

The pharmaceutical composition, food composition, cosmetic composition, and externally-applied dermal agent are as described above.

The present invention provides a method for treating an inflammatory disease, the method comprising administering an effective amount of *Lactococcus chungangensis* to a subject in need thereof.

The present invention provides a use of *Lactococcus chungangensis* for preparing an agent for treating an inflammatory disease, wherein the agent comprises *Lactococcus chungangensis* as an active ingredient.

The present invention provides a method for treating a bacterial infection, the method comprising administering an effective amount of *Lactococcus chungangensis* to a subject in need thereof.

The present invention provides a use of *Lactococcus chungangensis* for preparing an agent for treating a bacterial infection, wherein the agent comprises *Lactococcus chungangensis* as an active ingredient.

As used herein, the term "effective amount" refers collectively to an amount to alleviate a bacterial infection or an inflammatory disease when administered to a subject, and may encompass the amount capable of curing, substantially preventing, or improving the condition of such a disease. The term "subject" may be an animal, preferably a mammal, and especially, an animal including a human being, and may be a cell, a tissue, an organ, or the like, derived from an animal. The subject may be a patient in need of treatment.

The term "treatment" of the present invention refers collectively to alleviate the symptoms of bacterial infection or an inflammatory disease, may encompass curing, substantially preventing, or improving the condition of such a disease, and may include alleviating, curing, or preventing one or most of symptoms resulting from a bacterial infection or an inflammatory disease, but is not limited thereto.

Advantageous Effects

Therefore, the composition comprising *Lactococcus chungangensis* as an active ingredient according to the present invention has excellent effects of preventing and treating an inflammatory disease, inhibiting the release of main inflammation factors nitric oxide or prostaglandin $E_2$, inhibiting the release of main allergy-related factors β-hexosaminidase and histamine, and significantly inhibiting the production of skin disease-related cytokines and chemokines, and thus can be used as an agent for preventing or treating an inflammatory disease. Furthermore, the composition according to the present invention can be used in the prevention or treatment of a bacterial infection by exhibiting an antibacterial ability on *Staphylococcus aureus*, which is a microorganism causing a secondary infection of atopic dermatitis.

BRIEF DESCRIPTION OF THE DRAWINGS

FIG. 4A shows measurement results of β-hexosaminidase release upon the treatment of mast cell line, HMC-1 cells, with *Lactococcus chungangensis*.

FIG. 4B shows measurement results of histamine release upon the treatment of mast cell line, HMC-1 cells, with *Lactococcus chungangensis*.

FIG. 8 shows optical microscopic images of dorsal skin tissues and ear of each mouse in animal group, of which epidermis and dermis were subjected to H&E staining.

MODE FOR CARRYING OUT THE INVENTION

Figure 1:
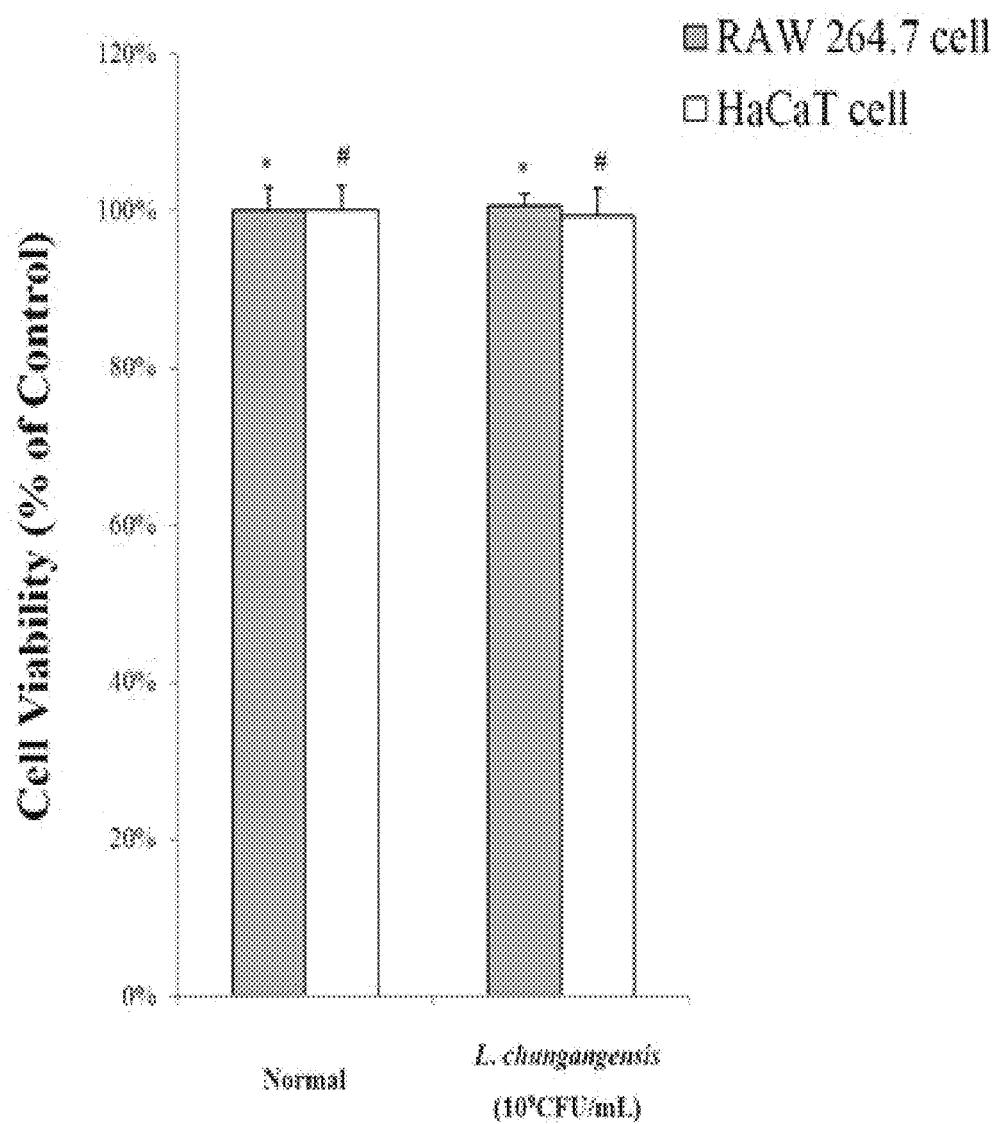
FIG. 1 shows results of cytotoxicity evaluation (cell viability measurement) of *Lactococcus chungangensis*.

Hereinafter, the present invention will be described in detail.

However, the following examples are merely for illustrating the present invention and are not intended to limit the scope of the present invention.

Statistical Analysis

In all test measurements, statistical analyses between test groups were performed by one-way ANOVA, and the significance test for the mean value among the groups was analyzed at $P<0.05$. A P value of 0.05 or less was symbolized as asterisk (*) in the drawings. In the results of human keratinocyte cell line, HaCaT cells, and NC/Nga mice, a p value of 0.05 or less was identified as sharp (#).

Example 1

*Lactococcus chungangensis* Culture

*Lactococcus chungangensis* is a strain isolated in the present inventors' laboratory, and isolated from activated sludge bubbles. The strain was deposited with the Korean Culture Type Collection. *Lactococcus chungangensis* was seeded in tryptic soy broth (TSB), and incubated in a 30° C. shaking incubator for 24 hours. Each cell density was measured using a microplate reader (model Infinite F200, Tecan, Mannedorf, Switzerland).

Example 2

Evaluation of Efficacy of *Lactococcus chungangensis* on Macrophages and Keratinocytes <2-1> Evaluation of Cytotoxicity of *Lactococcus Chungangensis* on RAW264.7 Cells and HaCaT Cells Cytotoxicity measurement of *Lactococcus chungangensis* cultured in Example 1 was carried out. Mouse macrophage line RAW264.7 cells and human keratinocyte cell line HaCaT cells were used for cytotoxicity measurement test, while cell viability assay was performed to determine cytotoxicity. RAW264.7 cells and HaCaT cells were subcultured for 4-5 passages a week, and were incubated in 20 μg/ml gentamycin solution and 10% fetal bovine serum (FBS)-containing Dulbecco's modified Eagle's medium (DMEM) at 37° C. in 5% $CO_2$ environment. RAW264.7 cells and HaCaT cells incubated for cell viability measurement were seeded in 24-well plate at density of 1×10$^5$ cells/well, and incubated for 24 hours. The cells were treated with *Lactococcus chungangensis* at 10$^9$ cell/ml in new DMEM not containing FBS, followed by incubation for 24 hours. For measurement of cell viability of cell lines, absorbance was determined at 590 nm by a microplate reader (model InfiniteF200, Tecan, M, Switzerland) using 3-(4,5-dimethylthiazol-2-yl)-2,5-diphenyltetrazolium bromide (MTT) reagent.

As shown in FIG. 1, the results confirmed that the cell viability of RAW264.7 cells and HaCaT cells treated with *Lactococcus chungangensis* was equal to the cell viability of the cells of the non-treatment group.

<2-2> Measurement of Anti-Inflammatory Activity of *Lactococcus chungangensis* in RAW264.7 Cells Anti-inflammatory activity measurement of *Lactococcus chungangensis* cultured in Example 1 was carried out. RAW264.7 cell were used for anti-inflammatory activity measurement like in <Example 2-1>. The cultured cells were seeded at density of 1×10$^5$ cells/well in 24-well plate, followed by incubation for 24 hours. For the induction of inflammation, LPS was added to new DMEM medium not containing FBS to have a concentration of 0.1 μg/ml, and the cells were treated with *Lactococcus chungangensis* at 10$^9$ cell/ml for 24 hours. After 24 hours, for the determination of NO production of cell lines in cell culture supernatant, Griess reagent was mixed with the supernatant at a ratio of 1:1, followed by reaction for 10 minutes, and then, absorbance was measured at 540 nm using a microplate reader (model InfiniteF200, Tecan, M, Switzerland). For the determination of $PGE_2$ production in the cell lines in the cell culture supernatant, the test was conducted according to the manual using Prostaglandin E2 Parameter™ Immunoassay Kit (R & D Systems, Minneapolis, Minn., USA). Absorbance was measured at 450 nm using a microplate reader to determine $PGE_2$ protein level.

Figure 2:
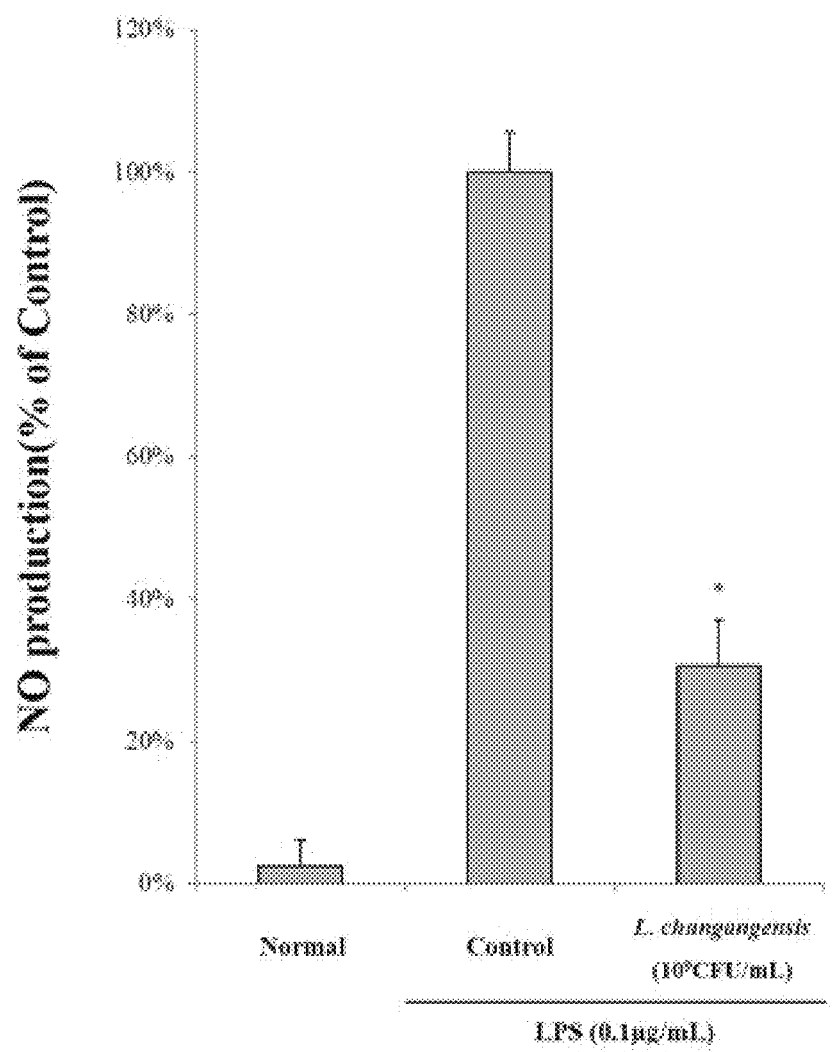
FIG. 2 shows measurement results of nitric oxide (NO) production upon the treatment of macrophages with *Lactococcus chungangensis*.
Figure 3:
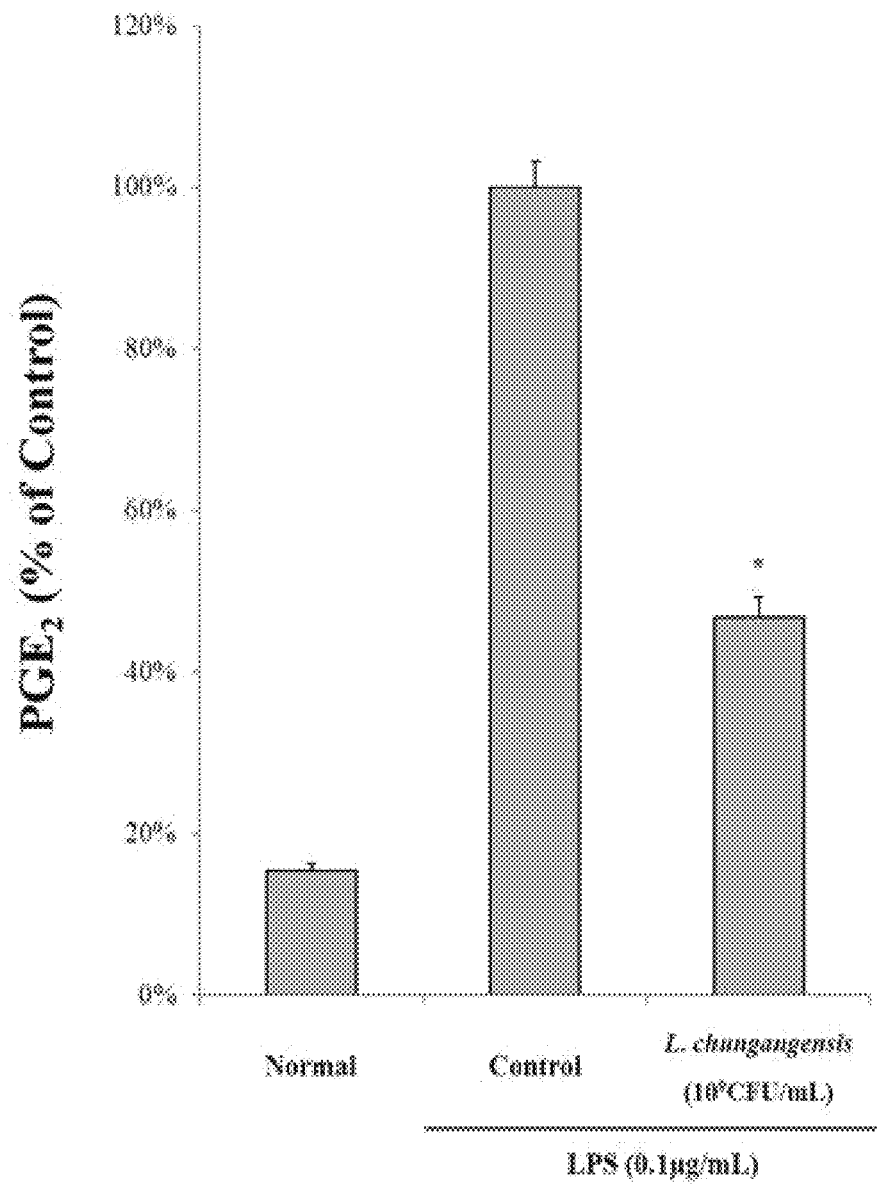
FIG. 3 shows measurement results of prostaglandin $E_2$ ($PGE_2$) production upon the treatment of macrophages with *Lactococcus chungangensis*.

As shown in FIGS. 2 and 3, the results confirmed that the NO production was remarkably reduced in LPS-stimulated RAW264.7 cells which were treated with *Lactococcus chungangensis* (FIG. 2) and that the $PGE_2$ production also showed a similar pattern (FIG. 3). Therefore, *Lactococcus chungangensis* was confirmed to inhibit an inflammatory response and have an anti-inflammatory effect. The results of the present study indicated that *Lactococcus chungangensis* showed high therapeutic efficacy on inflammation, suggesting that *Lactococcus chungangensis* is suitable for an anti-inflammatory composition, and further can be used for an anti-inflammatory therapeutic or pharmaceutical composition.

Example 3

Evaluation of In Vitro Anti-Allergy Efficacy of *Lactococcus chungangensis*

<3-1> Comparison of β-Hexosaminidase Release of Mast Cells (HMC-1) by *Lactococcus chungangensis*

β-hexosaminidase release is widely used as a main factor to exhibit activation and degranulation of mast cells. Therefore, in the present study, β-hexosaminidase release was measured using human mast cell line HMC-1 cells. HMC-1 cells were subcultured for 4-5 passages a week, and were incubated in 20 μg/ml gentamycin solution and 10% fetal bovine serum (FBS)-containing Iscove's modified Dulbecco's medium (IMDM) at 37° C. in 5% $CO_2$ environment. The incubated cells were seeded at density of 1×10$^6$ cells/well in 24-well plate, and treated with *Lactococcus chungangensis* 10$^9$ cell/ml, which was mixed with Tyrode's buffer (137 mM NaCl, 2.7 mM KCl, 1.8 mM $CaCl_2$, 1.1 mM $MgCl_2$, 11.9 mM $NaHCO_3$, 0.4 mM $NaH_2PO_4$, 5.6 mM glucose, pH 7.2), followed by incubation at 37° C. for 30 minutes. Thereafter, compound 48/80 was added at a concentration of 6 μg/ml, followed by incubation at 37° C. for 30 minutes. The reaction was terminated on ice, and centrifugation was conducted to deposit cells. Then, only the supernatant was taken, and 30 μl of the supernatant was transferred in 96 well plate, and 30 μl of 1 mM 4-p-nitrophenyl-N-acetyl-β-D-glucosaminide was added thereto, followed by incubation at 37° C. for 1 hour. Last, the reaction was stopped by 120 μl of stop solution (sodium bicarbonate, pH 10.2), and then absorbance was measured at 405 nm using a microplate reader.

After the HMC-1 cells were treated with *Lactococcus chungangensis*, compound 48/80 was used to induce the degranulation to release β-hexosaminidase, and the results are shown in FIG. 4A. As shown in FIG. 4, it was confirmed that *Lactococcus chungangensis* had an excellent β-hexosaminidase inhibitory effect, while inhibiting the β-hexosaminidase release by 65%.

<3-2> Comparison of Histamine Release of Mast Cells (HMC-1) by *Lactococcus chungangensis*

For the measurement of concentration of histamine released from human mast cell line HMC-1 cells, HMC-1 cells were incubated, and seeded at density of 1×10$^6$ cells/well in 24-well plate for 24 hours. After the incubation, the cells were treated with *Lactococcus chungangensis* at 10$^9$ cell/ml by the same method as in Example 3-1. Here, the cells were treated with compound 48/80 (10 μg/ml), followed by incubation for 20 minutes, and then the cell culture was harvested. The histamine levels in the cell culture were measured using a histamine assay ELISA kit (Cayman Chemical Company; Ann Arbor, Ill., USA), and the absorbance was determined at 450 nm by using a microplate reader.

After treatment with *Lactococcus chungangensis*, compound 48/80 was used to induce histamine in HMC-1 cells. The comparison results of the level of histamine released are shown in FIG. 4B. As can be confirmed in FIG. 4B, *Lactococcus chungangensis* showed a high histamine release inhibitory ability of 81%. Therefore, it can be seen that *Lactococcus chungangensis* showed high therapeutic efficacy on allergy. The results of the present study showed that *Lactococcus chungangensis* showed high therapeutic efficacy on allergy, indicating that *Lactococcus chungangensis* is suitable for an anti-allergy composition, and further can be used for allergy therapeutic or pharmaceutical composition.

Example 4

Evaluation of In Vivo Efficacy of *Lactococcus chungangensis* on Atopy-Induced BALE/c and NC/Nga Mice <4-1> Atopy Induction and Drug Treatment Mice were divided into a total of five groups, a non-treatment (normal) group, a DNCB group, a Tacrolimus skin application group, a *Lactococcus chungangensis* skin application group, and a *Lactococcus chungangensis* oral administration group. Then, 0.1 g of hair removal cream was applied on the back and neck of BALB/c and NC/Nga mice, respectively, and hairs were removed using soft tissue paper to avoid wounds. After the mice were left for 5 days to heal minor wounds, 1% DNCB 200 (acetone:olive oil=3:1) was applied to the back and ears three times a week for two weeks to induce atopy. After atopy induction, *Lactococcus chungangensis* was applied to diseased parts at $10^9$ cell/mouse twice a week for four weeks, while *Lactococcus chungangensis* was administered to oral cavity at $10^9$ cell/mouse twice a week for four weeks. For efficacy comparison, Tacrolimus in use as an atopy medicine was used. Tacrolimus was applied to atopy diseased parts at 100 mg/kg twice a week for four weeks.

<4-2> Visual Evaluation of Atopy-Induced BALE/c and NC/Nga Mice

Figure 5:
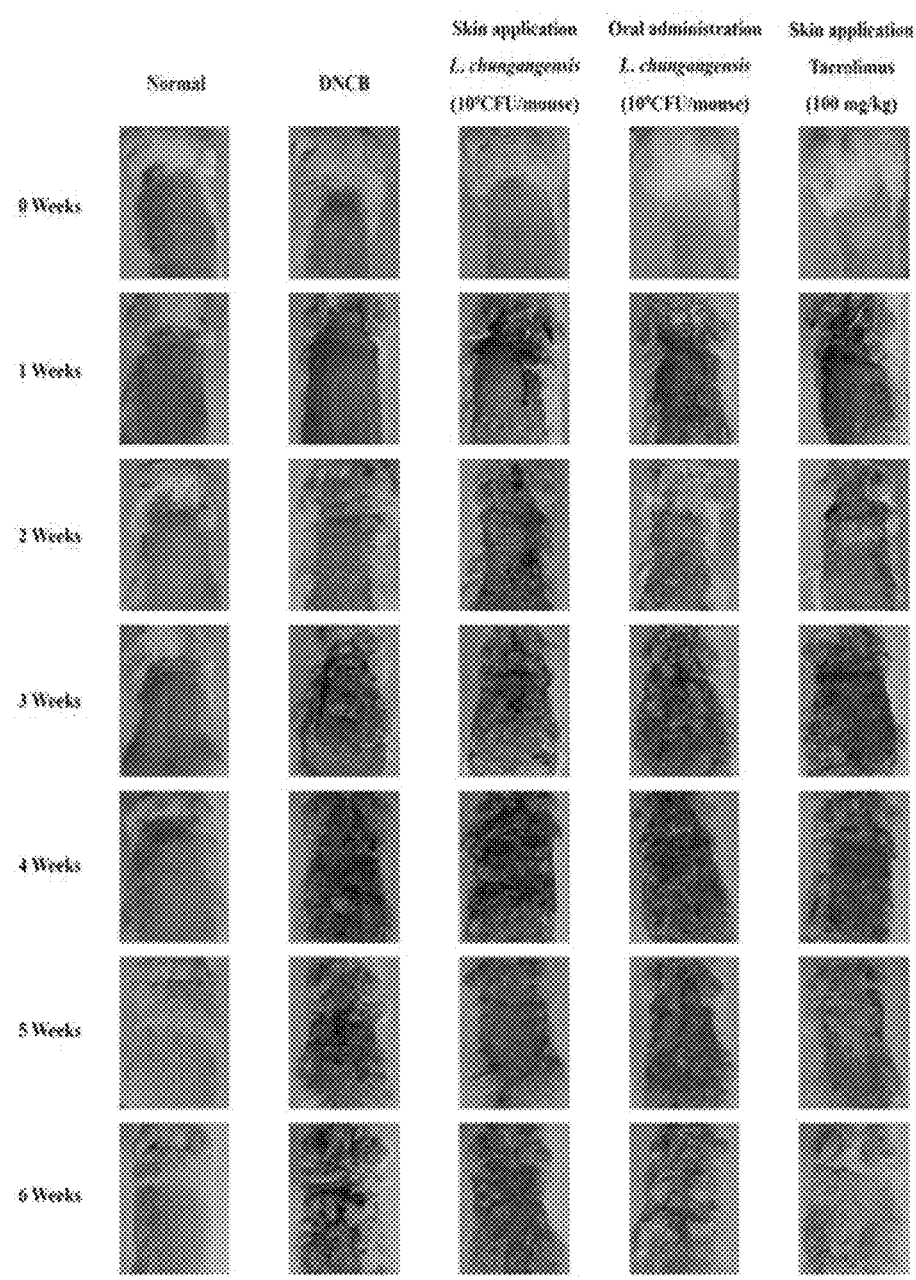
FIG. 5 shows photographic images of skin damage of BALB/c mice (Normal: normal BALB/c mouse, DNCB: atopy-induced BALB/c mouse, Skin application *L. chungangensis*: atopy-induced BALB/c mice subjected to skin application of *Lactococcus chungangensis*, Oral administration *L. chungangensis*: atopy-induced BALB/c mouse subjected to oral administration of *Lactococcus chungangensis*, Tacrolimus: atopy-induced BALB/c mouse subjected to skin application of Tacrolimus, hereinafter the same references have the same meanings in the following drawings).
Figure 6:
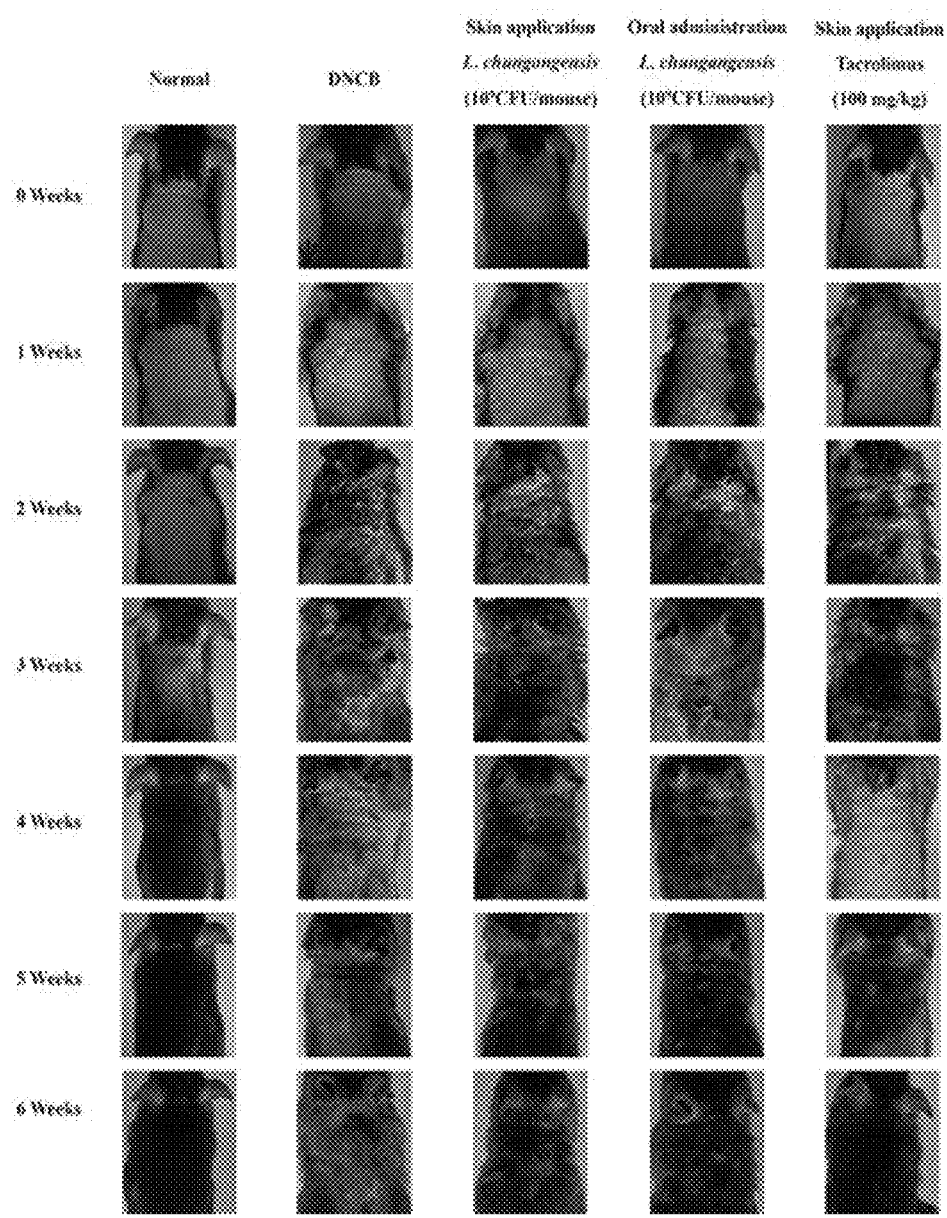
FIG. 6 shows photographic images of skin damage of NC/Nga mice.

Visual evaluation was conducted to determine a treatment effect in each of a Tacrolimus skin application group, a *Lactococcus chungangensis* skin application group, and a *Lactococcus chungangensis* oral administration group. Visual evaluation was conducted by evaluating the skin condition in four stages (0=absence, 1=mild, 2=moderate, 3=severe) according to the severity of erythema/hemorrhage, dryness/scarring, edema, and erosion/excoriation as evaluation indexes. A severity score of about 12 point or more was determined that the atopy symptoms reach the highest peak. The results are shown in Tables 1 to 5 for BALB/c mice, and Tables 6 to 10 for NC/Nga mice. The skin conditions that can be observed with the naked eye are shown in FIGS. 5 and 6.

Figure 7A:
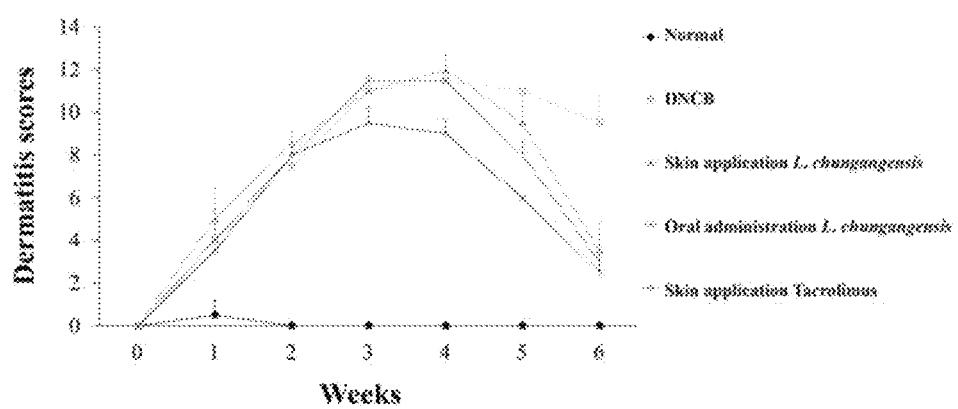
FIG. 7A shows measurement results of the number of scratching for 10 minutes by atopy-induced BALB/c mice (Dermatitis score: number of scratching by the mice).
Figure 7B:
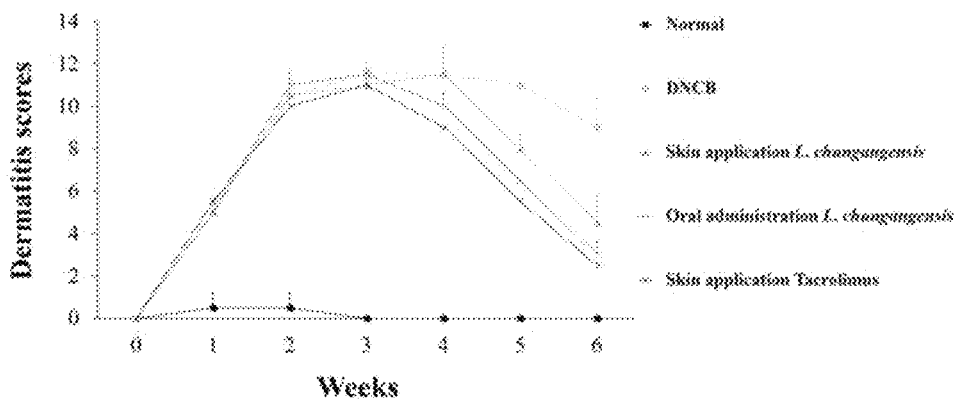
FIG. 7B shows measurement results of the number of scratching for 10 minutes by atopy-induced NC/Nga mice (Dermatitis score: number of scratching by the mice).

In addition, the number of scratching in BALB/c and NC/Nga mice for 10 minutes was measured, and the measurement results are shown in FIGS. 7A and 7B.

TABLE 1

Visual evaluation results of normal BALB/c mice (normal)

| | 1 Week | | 2 Weeks | | 3 Weeks | | 4 Weeks | | 5 Weeks | | 6 Weeks | |
|---|---|---|---|---|---|---|---|---|---|---|---|---|
| (—) | 1 | 2 | 3 | 4 | 5 | 6 | 7 | 8 | 9 | 10 | 11 | 12 |
| erythema/hemorrhage | 0 | 0 | 0 | 0 | 0 | 0 | 0 | 0 | 0 | 0 | 0 | 0 |
| dryness/scarring | 1 | 0 | 0 | 0 | 0 | 0 | 0 | 0 | 0 | 0 | 0 | 0 |
| edema | 0 | 0 | 0 | 0 | 0 | 0 | 0 | 0 | 0 | 0 | 0 | 0 |
| erosion/excoriation | 0 | 0 | 0 | 0 | 0 | 0 | 0 | 0 | 0 | 0 | 0 | 0 |
| Total | 1 | 0 | 0 | 0 | 0 | 0 | 0 | 0 | 0 | 0 | 0 | 0 |
| Mean | 0.5 | | 0 | | 0 | | 0 | | 0 | | 0 | |

TABLE 2

Visual evaluation results of DNCB-induced atopic BALB/c mice

| | 1 Week | | 2 Weeks | | 3 Weeks | | 4 Weeks | | 5 Weeks | | 6 Weeks | |
|---|---|---|---|---|---|---|---|---|---|---|---|---|
| DNCB | 1 | 2 | 3 | 4 | 5 | 6 | 7 | 8 | 9 | 10 | 11 | 12 |
| erythema/hemorrhage | 0 | 0 | 2 | 2 | 3 | 3 | 3 | 2 | 3 | 3 | 3 | 2 |
| dryness/scarring | 2 | 2 | 2 | 2 | 3 | 3 | 3 | 3 | 3 | 3 | 3 | 2 |
| edema | 0 | 1 | 1 | 2 | 3 | 2 | 3 | 3 | 2 | 3 | 2 | 2 |
| erosion/excoriation | 1 | 2 | 2 | 2 | 2 | 3 | 3 | 3 | 3 | 2 | 3 | 2 |
| Total | 3 | 5 | 7 | 8 | 11 | 11 | 12 | 11 | 11 | 11 | 11 | 8 |
| Mean | 4 | | 7.5 | | 11 | | 11.5 | | 11 | | 9.5 | |

TABLE 3

Visual evaluation results of BALB/c mice subjected to skin application of atopy medicine (Tacrolimus) after DNCB-induced atopy

| DNCB + tacrolimus | 1 Week | | 2 Weeks | | 3 Weeks | | 4 Weeks | | 5 Weeks | | 6 Weeks | |
|---|---|---|---|---|---|---|---|---|---|---|---|---|
| skin application | 1 | 2 | 3 | 4 | 5 | 6 | 7 | 8 | 9 | 10 | 11 | 12 |
| erythema/hemorrhage | 2 | 2 | 2 | 2 | 3 | 3 | 3 | 3 | 2 | 1 | 1 | 0 |
| dryness/scarring | 1 | 1 | 2 | 2 | 2 | 2 | 3 | 1 | 2 | 2 | 1 | 1 |
| edema | 0 | 1 | 2 | 2 | 3 | 2 | 2 | 2 | 2 | 1 | 1 | 0 |
| erosion/excoriation | 1 | 2 | 2 | 2 | 3 | 3 | 3 | 3 | 1 | 1 | 1 | 0 |
| Total | 4 | 6 | 8 | 8 | 11 | 10 | 10 | 9 | 7 | 5 | 4 | 1 |
| Mean | 5 | | 8 | | 10.5 | | 9.5 | | 6 | | 2.5 | |

TABLE 4

Visual evaluation results of BALB/c mice subjected to skin application of *Lactococcus chungangensis* after DNCB-induced atopy

| DNCB + *Lactococcus chungangensis* | 1 Week | | 2 Weeks | | 3 Weeks | | 4 Weeks | | 5 Weeks | | 6 Weeks | |
|---|---|---|---|---|---|---|---|---|---|---|---|---|
| skin application | 1 | 2 | 3 | 4 | 5 | 6 | 7 | 8 | 9 | 10 | 11 | 12 |
| erythema/hemorrhage | 1 | 1 | 2 | 3 | 3 | 3 | 3 | 3 | 3 | 2 | 1 | 0 |
| dryness/scarring | 2 | 2 | 2 | 2 | 3 | 3 | 3 | 3 | 3 | 2 | 2 | 1 |
| edema | 0 | 1 | 2 | 2 | 2 | 2 | 3 | 3 | 2 | 3 | 1 | 0 |
| erosion/excoriation | 1 | 2 | 2 | 2 | 3 | 3 | 3 | 3 | 2 | 2 | 2 | 0 |
| Total | 4 | 6 | 8 | 9 | 11 | 11 | 12 | 12 | 10 | 9 | 6 | 1 |
| Mean | 5 | | 8.5 | | 11 | | 12 | | 9.5 | | 3.5 | |

TABLE 5

Visual evaluation results of NC/Nga mice subjected to oral application of *Lactococcus chungangensis* after DNCB-induced atopy

| DNCB + *Lactococcus chungangensis* oral | 1 Week | | 2 Weeks | | 3 Weeks | | 4 Weeks | | 5 Weeks | | 6 Weeks | |
|---|---|---|---|---|---|---|---|---|---|---|---|---|
| administration | 1 | 2 | 3 | 4 | 5 | 6 | 7 | 8 | 9 | 10 | 11 | 12 |
| erythema/hemorrhage | 1 | 1 | 2 | 2 | 3 | 3 | 3 | 2 | 2 | 2 | 1 | 0 |
| dryness/scarring | 1 | 1 | 3 | 2 | 3 | 3 | 3 | 3 | 2 | 2 | 1 | 1 |
| edema | 1 | 1 | 1 | 2 | 3 | 2 | 3 | 3 | 2 | 2 | 1 | 0 |
| erosion/excoriation | 1 | 1 | 2 | 2 | 3 | 3 | 3 | 3 | 2 | 2 | 1 | 1 |
| Total | 4 | 4 | 8 | 8 | 12 | 11 | 12 | 11 | 8 | 8 | 4 | 2 |
| Mean | 4 | | 8 | | 11.5 | | 11.5 | | 8 | | 3 | |

TABLE 6

Visual evaluation results of normal NC/Nga mice

|  | 1 Week | | 2 Weeks | | 3 Weeks | | 4 Weeks | | 5 Weeks | | 6 Weeks | |
| --- | --- | --- | --- | --- | --- | --- | --- | --- | --- | --- | --- | --- |
| (—) | 1 | 2 | 3 | 4 | 5 | 6 | 7 | 8 | 9 | 10 | 11 | 12 |
| erythema/hemorrhage | 0 | 0 | 0 | 0 | 0 | 0 | 0 | 0 | 0 | 0 | 0 | 0 |
| dryness/scarring | 1 | 0 | 1 | 0 | 0 | 0 | 0 | 0 | 0 | 0 | 0 | 0 |
| edema | 0 | 0 | 0 | 0 | 0 | 0 | 0 | 0 | 0 | 0 | 0 | 0 |
| erosion/excoriation | 0 | 0 | 0 | 0 | 0 | 0 | 0 | 0 | 0 | 0 | 0 | 0 |
| Total | 1 | 0 | 1 | 0 | 0 | 0 | 0 | 0 | 0 | 0 | 0 | 0 |
| Mean | 0.5 | | 0.5 | | 0 | | 0 | | 0 | | 0 | |

TABLE 7

Visual evaluation results of DNCB-induced atopic NC/Nga mice

|  | 1 Week | | 2 Weeks | | 3 Weeks | | 4 Weeks | | 5 Weeks | | 6 Weeks | |
| --- | --- | --- | --- | --- | --- | --- | --- | --- | --- | --- | --- | --- |
| DNCB | 1 | 2 | 3 | 4 | 5 | 6 | 7 | 8 | 9 | 10 | 11 | 12 |
| erythema/hemorrhage | 1 | 1 | 3 | 3 | 3 | 3 | 3 | 3 | 3 | 3 | 3 | 2 |
| dryness/scarring | 2 | 2 | 3 | 3 | 3 | 3 | 3 | 3 | 3 | 3 | 3 | 2 |
| edema | 1 | 1 | 3 | 2 | 3 | 2 | 3 | 3 | 2 | 3 | 2 | 2 |
| erosion/excoriation | 1 | 2 | 2 | 2 | 3 | 3 | 3 | 2 | 3 | 2 | 2 | 2 |
| Total | 5 | 6 | 11 | 10 | 12 | 11 | 12 | 11 | 11 | 11 | 10 | 8 |
| Mean | 5.5 | | 10.5 | | 11.5 | | 11.5 | | 11 | | 9 | |

TABLE 8

Visual evaluation results of NC/Nga mice subjected to skin application of atopy medicine (Tacrolimus) after DNCB-induced atopy

| DNCB + Atopy | 1 Week | | 2 Weeks | | 3 Weeks | | 4 Weeks | | 5 Weeks | | 6 Weeks | |
| --- | --- | --- | --- | --- | --- | --- | --- | --- | --- | --- | --- | --- |
| medicine | 1 | 2 | 3 | 4 | 5 | 6 | 7 | 8 | 9 | 10 | 11 | 12 |
| erythema/hemorrhage | 1 | 1 | 3 | 3 | 3 | 3 | 3 | 3 | 3 | 3 | 3 | 2 |
| dryness/scarring | 2 | 2 | 3 | 3 | 3 | 3 | 3 | 3 | 3 | 3 | 3 | 2 |
| edema | 1 | 1 | 3 | 2 | 3 | 2 | 3 | 3 | 2 | 3 | 2 | 2 |
| erosion/excoriation | 1 | 2 | 2 | 2 | 3 | 3 | 3 | 2 | 3 | 2 | 2 | 2 |
| Total | 5 | 6 | 11 | 10 | 12 | 11 | 12 | 11 | 11 | 11 | 10 | 8 |
| Mean | 5.5 | | 10.5 | | 11.5 | | 11.5 | | 11 | | 9 | |

TABLE 9

Visual evaluation results of NC/Nga mice subjected to skin application of *Lactococcus chungangensis* after DNCB-induced atopy

| DNCB + *Lactococcus chungangensis* | 1 Week | | 2 Weeks | | 3 Weeks | | 4 Weeks | | 5 Weeks | | 6 Weeks | |
| --- | --- | --- | --- | --- | --- | --- | --- | --- | --- | --- | --- | --- |
| skin application | 1 | 2 | 3 | 4 | 5 | 6 | 7 | 8 | 9 | 10 | 11 | 12 |
| erythema/hemorrhage | 1 | 1 | 2 | 3 | 3 | 3 | 3 | 3 | 2 | 2 | 1 | 1 |
| dryness/scarring | 2 | 2 | 3 | 3 | 3 | 3 | 3 | 3 | 2 | 2 | 1 | 1 |
| edema | 1 | 1 | 3 | 3 | 3 | 2 | 3 | 3 | 2 | 2 | 2 | 1 |
| erosion/excoriation | 1 | 1 | 2 | 2 | 2 | 3 | 2 | 3 | 2 | 2 | 1 | 1 |
| Total | 5 | 5 | 10 | 11 | 11 | 11 | 11 | 12 | 8 | 8 | 5 | 4 |
| Mean | 5 | | 10.5 | | 11 | | 11.5 | | 8 | | 4.5 | |

TABLE 10

Visual evaluation results of NC/Nga mice subjected to oral administration of *Lactococcus chungangensis* after DNCB-induced atopy

| DNCB + *Lactococcus chungangensis* oral | 1 Week | | 2 Weeks | | 3 Weeks | | 4 Weeks | | 5 Weeks | | 6 Weeks | |
| --- | --- | --- | --- | --- | --- | --- | --- | --- | --- | --- | --- | --- |
| administration | 1 | 2 | 3 | 4 | 5 | 6 | 7 | 8 | 9 | 10 | 11 | 12 |
| erythema/hemorrhage | 1 | 1 | 3 | 3 | 3 | 3 | 3 | 3 | 2 | 2 | 0 | 0 |
| dryness/scarring | 2 | 2 | 3 | 3 | 3 | 3 | 3 | 3 | 2 | 1 | 1 | 1 |
| edema | 1 | 1 | 3 | 3 | 3 | 2 | 2 | 2 | 2 | 2 | 1 | 1 |
| erosion/excoriation | 1 | 1 | 2 | 2 | 3 | 3 | 2 | 2 | 1 | 1 | 1 | 1 |
| Total | 5 | 5 | 11 | 11 | 12 | 11 | 10 | 10 | 7 | 6 | 3 | 3 |
| Mean | 5 | | 11 | | 11.5 | | 10 | | 6.5 | | 3 | |

After BALB/c mice were treated with DNCB for 2 weeks (0-2 weeks in FIG. 3) to induce atopy, the skin damage condition was observed by the naked eye for an atopy medicine Tacrolimus 100 mg/kg diseased part application group, a *Lactococcus chungangensis* $10^9$ cell/mouse diseased part application group, and a *Lactococcus chungangensis* $10^9$ cell/mouse oral administration group, and the results are shown in FIG. 5 and Tables 1 to 5. The atopy-induced skin had several symptoms, such as the formation of dead skin cells caused by dry skin, systemic erythema, and exudative crusts, bleeding, and edema. The skin condition was remarkably improved in the Tacrolimus skin application group and the *Lactococcus chungangensis* oral administration group. On the contrary, it was confirmed that the skin condition was improved slowly when observed by the naked eye although the improvement was slower in the *Lactococcus chungangensis* skin application group than the *Lactococcus chungangensis* oral administration group. A similar tendency was also observed in the evaluation of the number of scratching in BALB/c mice. Especially, the number of scratching in the *Lactococcus chungangensis* oral administration group was remarkably reduced at the same level as that in Tacrolimus treatment group. After NC/Nga mice were also treated with DNCB for 2 weeks (0-2 weeks in FIG. 3) to induce atopy, the skin damage condition was observed by the naked eye in the same manner for an atopy medicine Tacrolimus 100 mg/kg diseased part application group, a *Lactococcus chungangensis* $10^9$ cell/mouse diseased part application group, and a *Lactococcus chungangensis* $10^9$ cell/mouse oral administration group, and the results are shown in FIG. 6 and Tables 6 to 10. Several symptoms, such as the formation of dead skin cells caused by dry skin, systemic erythema, and exudative crusts, bleeding, and edema, were also observed in NC/Nga mice. A faster healing performance after the treatment with test materials was observed in NC/Nga mice, compared with BALB/c mice. In conclusion, it could be seen that the *Lactococcus chungangensis* oral administration groups of BALB/c and NC/Nga mice show high therapeutic efficacy on the skin damage caused by DNCB treatment.

<4-3> Histopathological Test

After the treatment of test materials, the dorsal skin tissue (1.5×1.5 cm) and ears of BALB/c mice and NC/Nga mice of the test and control groups were taken off, and fixed in 10% paraformaldehyde for 24 hours. The tissues were sufficiently hardened in paraffin, and sliced into five pieces to prepare slide glasses. Staining was conducted using haematoxylin-eosin (H&E) by a known method, and the epidermal and dermal thicknesses were observed, and the results are shown in FIG. 8.

As shown in FIG. 8, dead skin cell exfoliation, epidermal hypertrophy, and hyperkeratosis were observed in the epidermis of DNCB-induced atopic BALB/c mice and NC/Nga mice. In contrast, it was verified that dead skin cell exfoliation, epidermal hypertrophy, and hyperkeratosis were significantly reduced in the atopy medicine Tacrolimus skin application and the *Lactococcus chungangensis* oral administration BALB/c and NC/Nga mice groups, and that dead skin cell exfoliation, epidermal hypertrophy, and hyperkeratosis were somewhat reduced in the *Lactococcus chungangensis* skin application group compared with DNCB-induced atopic mice.

<4-4> Immunoglobulin IgE Measurement

After the ending of the treatment with test materials, BALB/c and NC/Nga mice of the five groups were sacrificed, and blood was collected from the heart. Serum was isolated from the blood to measure IgE. Specifically, under the use of an IgE ELISA Kit (BD Biosciences, San Diego, Calif.), antibody was diluted in a buffer solution, and allowed to adhere a 96-well plate, and the plate was allowed to stand overnight at 4° C., and the test was conducted according to the manual. Absorbance was measured at 450 nm using a microplate reader to determine IgE protein level.

Figure 9:
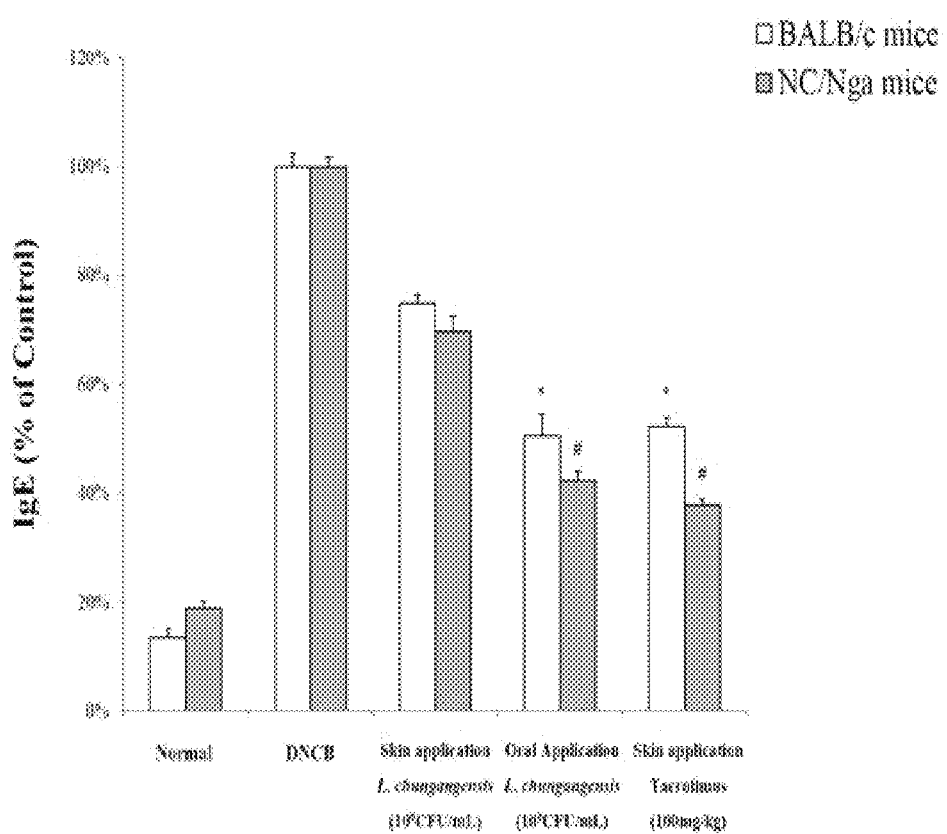
FIG. 9 shows comparative evaluation results of immunoglobulin IgE production in serum isolated from the blood of each mouse in animal group.

The level of IgE mediating atopic diseases was measured from the serum, which was isolated from the blood taken from the heart of each of BALB/c and NC/Nga mice, using an IgE ELISA Kit, and the results are shown in FIG. 9. As a result of investigating the level of IgE in the BALB/c mice and NC/Nga mice treated with test materials, the production of IgE was significantly inhibited in the Tacrolimus skin application group and the *Lactococcus chungangensis* oral administration group. In the BALB/c mice, the production of IgE was inhibited by 48% in the Tacrolimus skin application group and by 49% in the *Lactococcus chungangensis* oral administration group, compared with the DNCB-induced group. In addition, it was verified that the *Lactococcus chungangensis* skin application group also showed a low level of inhibition, about 25%. Also in the NC/Nga mice, the production of IgE was inhibited by 62% in the Tacrolimus skin application group, by 58% in the *Lactococcus chungangensis* oral administration group, and by 30% in the *Lactococcus chungangensis* skin application group. The above results indicated that *Lactococcus chungangensis* can have an effect on atopic diseases.

<4-5> Chemokine and Cytokine Measurement

Figure 10A:
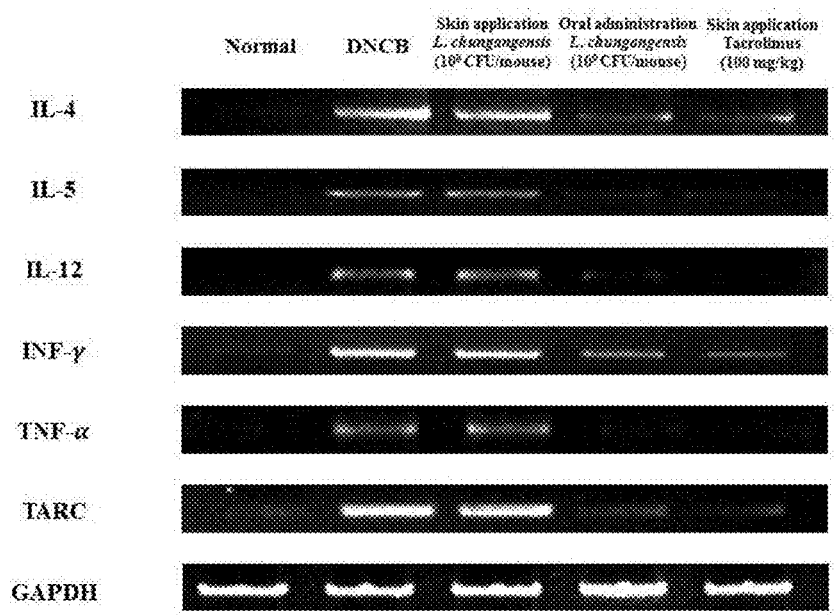
FIG. 10A shows PCR evaluation results of mRNA levels of allergy-related chemokines and cytokines (IL-4, IL-5, IL-12, IFN-γ, TNF-α, and TARC) in the skin tissue of each mouse in animal group.
Figure 10B:
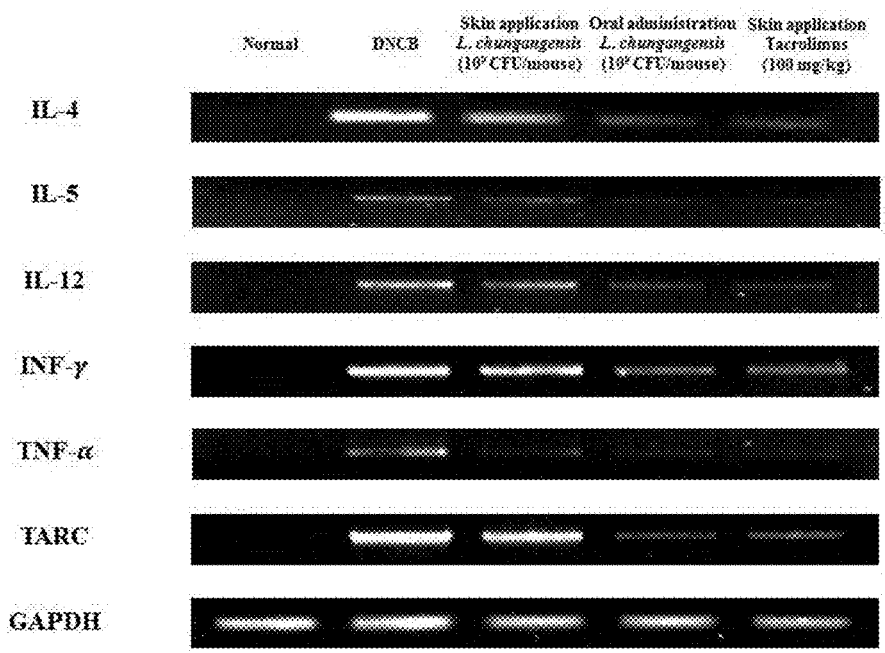
FIG. 10B shows PCR evaluation results of mRNA levels of allergy-related chemokines and cytokines (IL-4, IL-5, IL-12, IFN-γ, TNF-α, and TARC) in the skin tissue of each mouse in animal group.

After the ending of the treatment of the BALB/c and NC/Nga mice with test materials, the BALB/c and NC/Nga mice of the DNCB-induced atopic control group, the Tacrolimus skin application group, the *Lactococcus chungangensis* skin application group, and the *Lactococcus chungangensis* oral administration group were sacrificed. The skin tissues were extracted, and Trizol was added thereto, and the skin tissues were homogenized using a homogenizer until dissolved, and RNA was extracted from the homogenized tissues. Specifically, Trizol was added to the skin tissues extracted from BALB/c mice and NC/Nga mice of each of the control and test groups, and chloroform ($CHCl_3$) was added thereto and mixed. Then, the mixture was allowed to stand for 10 minutes and centrifuged. The centrifuged supernatant was recovered, mixed with the same amount of 2-propanol, allowed to stand for 10 minutes, centrifuged again, washed with 80% EtOH, and dried, to thereby obtain RNA. cDNA was obtained by reverse transcription PCR using AMV reverse transcriptase, dNTP (Promega, Madison, Wis.), EX Taq DNA polymerase (Takara Shuzou, Kyoto, Japan), and the obtained cDNA was used to investigate the mRNA expression levels of atopic-related chemokines and cytokines. Specifically, PCR was performed using the primer pairs described in Table 5 below for chemokines and cytokines IL-4, IL-5, IL-12, IFN-γ, TNF-α, and TARC and control GAPDH, respectively. The PCR was performed for 30 cycles of 1 minute at 94° C., 30 seconds at 95° C., 30 seconds at 55-65° C., and 3 minutes at 70° C. After the PCR, the PCR products were analyzed using 1.5% agarose gel electrophoresis and imaged using GelDoc™ XR+(Bio-Rad, Hercules, Calif., USA), and the results are shown in FIGS. 10A and 10B. The primers used in the above PCR were prepared by Macrogen. Table 11 below shows nucleotide sequences of primers used in reverse transcription PCR.

In addition, the protein level changes of IL-4, IL-5, IL-12, IFN-γ, TNF-α, and TARC in the serum isolated from the blood taken from the heart of each of BALB/c mice and NC/Nga mice were measured using IL-4 Quantikine Immunoassay Kit, IL-5 Quantikine Immunoassay Kit, IL-12 Quantikine Immunoassay Kit, TNF-α Quantikine Immunoassay Kit, CCL17/TARC Quantikine Immunoassay Kit (R&D Systems, Minneapolis, Minn., USA), respectively, and the absorbance was determined at 450 nm by using a microplate reader.

TABLE 11

Nucleotide sequences of primers used for PCR

| Gene | Direction | Primer nucleotide sequences (5′ to 3′) | SEQ ID number |
|---|---|---|---|
| IL-4 | Sense | TCAACCCCCAGCTAGTTGTCA | 1 |
|  | antisense | CATCGAAAAGCCCGAAAGAG | 2 |
| IL-5 | Sense | AGCACAGTGGTGAAAGAGACCTT | 3 |
|  | antisense | TCCAATGCATAGCTGGTGATTT | 4 |
| IL-12 | Sense | GACACGCCTGAAGAAGATGAC | 5 |
|  | antisense | CGCCATTCCACATGTCACTGC | 6 |
| IFNγ | Sense | AACGCTACACACTGCATCT | 7 |
|  | antisense | GAGCTCATTGAATGCTTGG | 8 |
| TNFα | sense | CAGGCGGTGCCTATGTCTC | 9 |
|  | antisense | CGATCACCCCGAAGTTCAGTAG | 10 |

TABLE 11-continued

Nucleotide sequences of primers used for PCR

| Gene | Direction | Primer nucleotide sequences (5' to 3') | SEQ ID number |
|---|---|---|---|
| TARC | sense | CAGGAAGTTGGTGAGCTGGTATA | 11 |
|  | antisense | TTGTGTTCGCCTGTAGTGCATA | 12 |
| GAPDH | sense | AAGCTGTGGCGTGATGGCCG | 13 |
|  | antisense | TGGGCCCTCAGATGCCTGCT | 14 |

The BALB/c mice and NC/Nga mice of the DNCB-induced atopy control group, the Tacrolimus skin application group, the *Lactococcus chungangensis* skin application, and the *Lactococcus chungangensis* oral administration group were sacrificed. RNA from the extracted tissues was investigated using chemokine- and cytokine-specific primers, respectively. As a result, it was investigated that the expression levels of IL-4, IL-5, IL-12, IFN-γ, TNF-α, and TARC in the Tacrolimus skin application group and the *Lactococcus chungangensis* oral administration group, compared with the DNCB-induced atopy mice (FIG. 10).

Figure 11A:
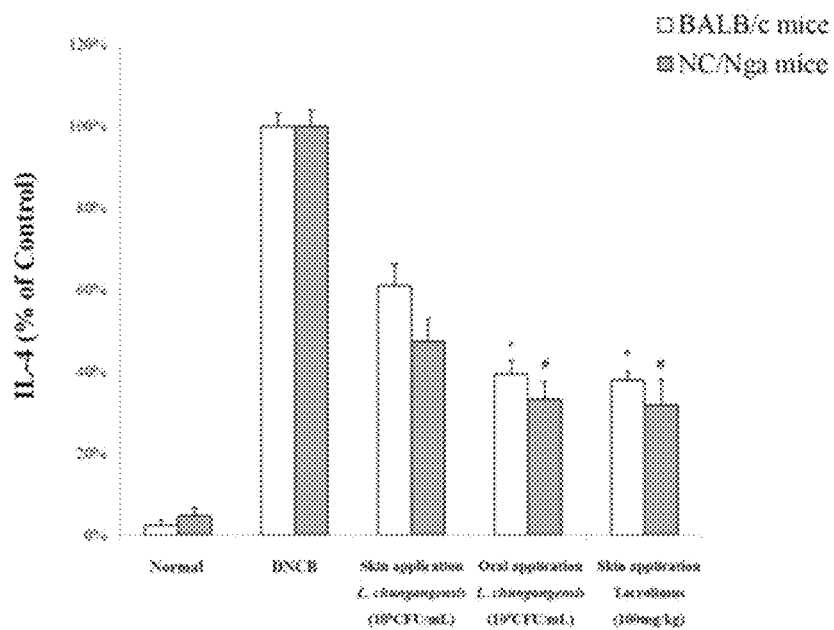
FIG. 11A shows evaluation results of IL-4 protein level of serum isolated from blood of each mouse in animal group.
Figure 11B:
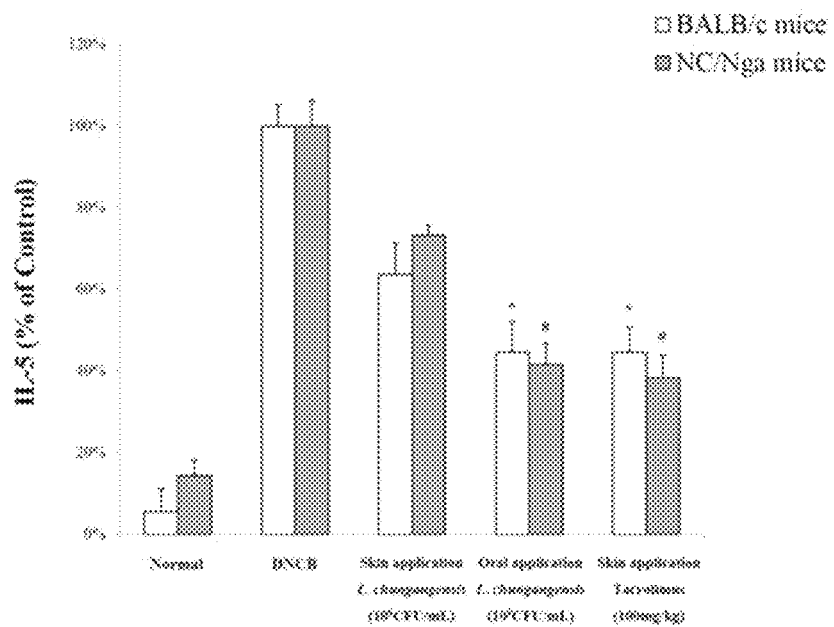
FIG. 11B shows evaluation results of IL-5 protein level of serum isolated from blood of each mouse in animal group.
Figure 12A:
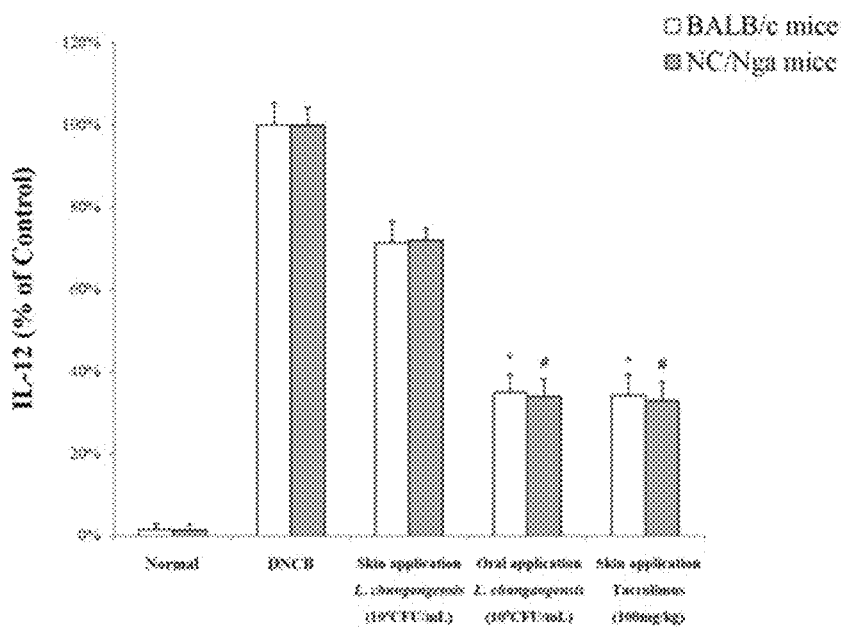
FIG. 12A shows evaluation results of IL-12 protein level of serum isolated from blood of each mouse in animal group.
Figure 12B:
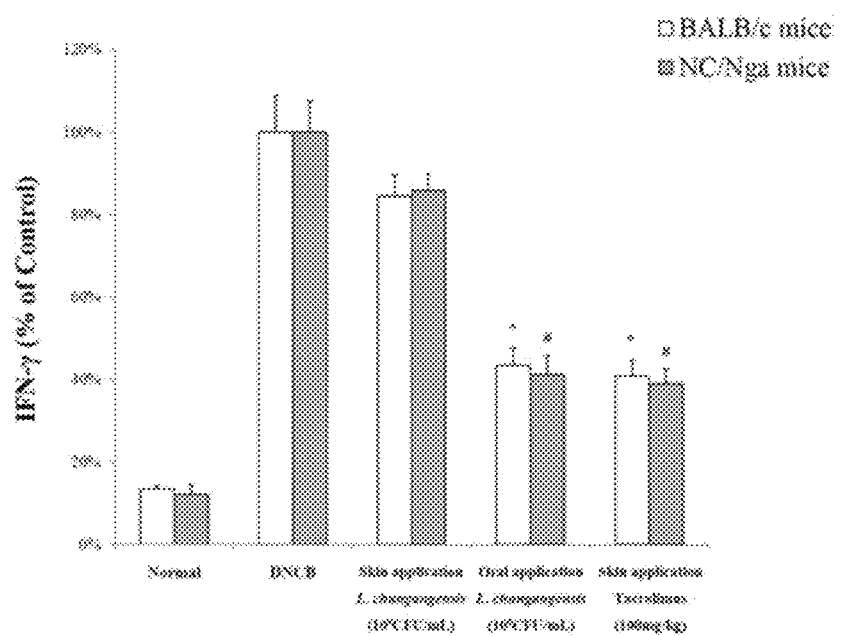
FIG. 12B shows evaluation results of IFN-γ protein level of serum isolated from blood of each mouse in animal group.
Figure 13A:
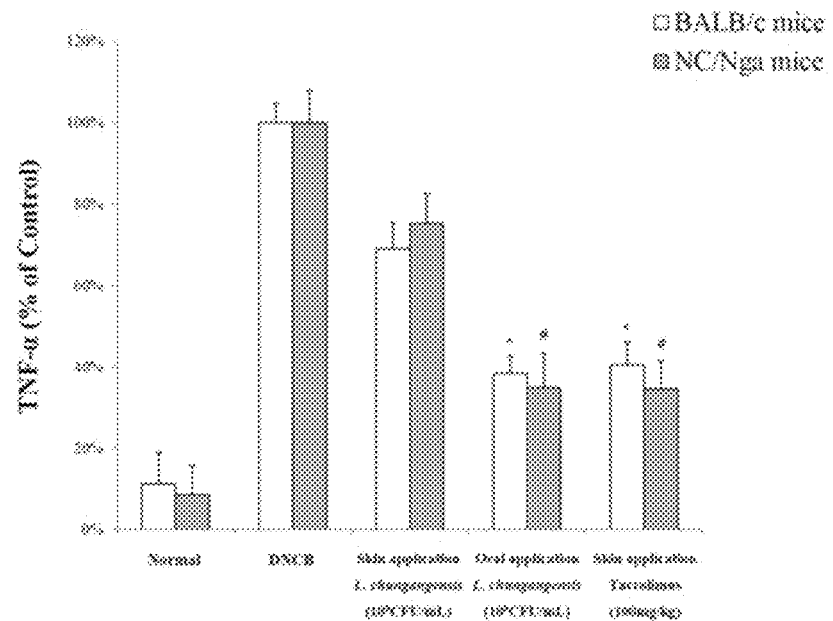
FIG. 13A shows evaluation results of TNF-α protein level of serum isolated from blood of each mouse in animal group.
Figure 13B:
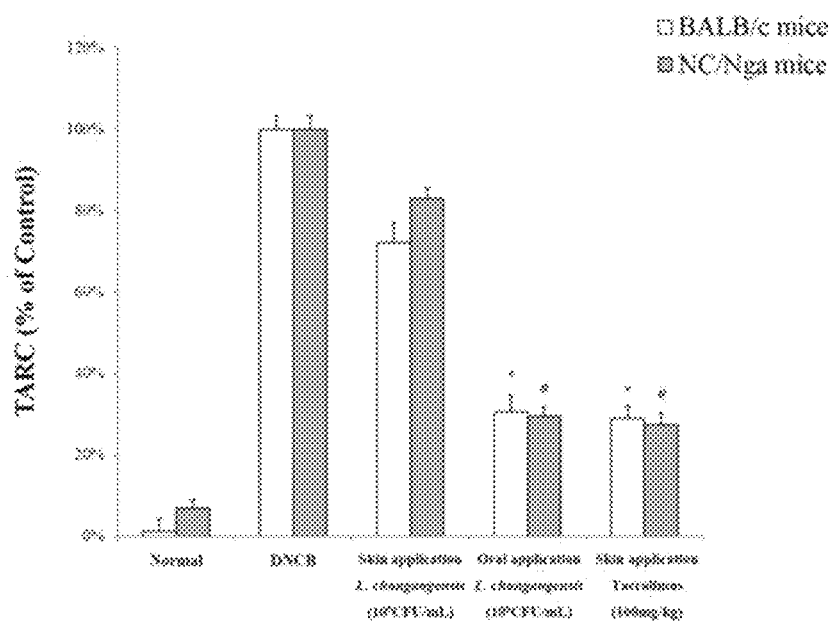
FIG. 13B shows evaluation results of TARC protein level of serum isolated from blood of each mouse in animal group.

In addition, the levels of chemokines and cytokines mediating atopic diseases were measured from the serum isolated from the blood taken from the heart of each of BALB/c mice and NC/Nga mice by using ELISA Kit. As a result, it was verified that the protein levels of IL-4, IL-5, IL-12, IFN-γ, TNF-α, and TARC were significantly reduced in the Tacrolimus skin application group and the *Lactococcus chungangensis* oral administration group, compared with the DNCB-induced atopy mice (FIGS. 11 to 13). It was verified that the protein levels of IL-4, IL-5, IL-12, IFN-γ, TNF-α, and TARC were also slightly reduced in the *Lactococcus chungangensis* skin application group. Therefore, the results indicated that *Lactococcus chungangensis* of the present invention can have an effect on atopy at a similar level to Tacrolimus, and further, can be used for atopy therapeutic or pharmaceutical composition.

Example 5

Verification of Antibacterial Activity of *Lactococcus chungangensis* on *Staphylococcus aureus* as Microorganism Causing Secondary Infection of Atopic Dermatitis <5-1> Preparation of Test Microorganisms

*Lactococcus chungangensis* was cultured using tryptic soy broth (TSB) in a 30° C. shaking incubator for 24 hours. Antibacterial test was conducted. In the test, *Staphylococcus* sp. bacterium (*Staphylococcus aureus* NCCP 14780) was obtained from the National Institutes of Natural Resources Collection (NCCP), which is a well-known depository institution.

<5-2> Measurement of Antibacterial Activity of *Lactococcus chungangensis* on *Staphylococcus aureus* as Microorganism Causing Secondary Infection of Atopic Dermatitis For the measurement of antibacterial activity of *Lactococcus chungangensis*, *Lactococcus* was cultured in a 30° C. incubator for 24 hours. The obtained line *Staphylococcus* sp. bacterium was cultured using brain heart infusion (BHI) medium in a 37° C. incubator for 24 hours. After the cultured *Lactococcus chungangensis* was transferred to another tryptic soy broth (TSB), the cultured *Staphylococcus* sp. bacterium was controlled to 5×10$^7$ cells per culture dish, and 7 ml of unhardened BHI agar medium was poured, and then well hardened, followed by incubation in a 30° C. incubator for 24 hours. A growth inhibition zone, that is, a clear zone of bacteria generated after incubation was checked, and the diameter of the clear zone was measured, and the results are shown in Table 12.

TABLE 12

Measurement of antibacterial activity of *Lactococcus chungangensis*

|  |  | Clear zone (mm) | | | |
|---|---|---|---|---|---|
| Microorganism | Strain | 1 | 2 | 3 | Average |
| *Staphylococcus aureus* | NCCP14780 | 30 | 40 | 40 | 36.7 |

As shown in Table 12, it could be seen that *Lactococcus chungangensis* exhibited antibacterial activity on *Staphylococcus* sp. bacterium. The results indicated that *Lactococcus chungangensis* can protect against secondary infection of atopic dermatitis by *Staphylococcus* sp. bacterium and is safer than an antibacterial agent, and thus can be used for atopy treatment or as a pharmaceutical composition.

Preparative Example 1

Preparation of Externally-Applied Dermal Agent

<1-1> Preparation of Ointment

Ointment was prepared by mixing the ingredients shown below following a method that is conventionally conducted in the art.

| *Lactococcus chungangensis* | 5.00 wt % |
|---|---|
| Capric/caprylic triglyceride | 10.00 wt % |
| Liquid paraffin | 10.00 wt % |
| Sorbitan sesquiunorate | 6.00 wt % |
| Octyldodeces-25 | 9.00 wt % |
| Cetyl ethylhexanoate | 10.00 wt % |
| Squalane | 1.00 wt % |
| Salicylic acid | 1.00 wt % |
| Glycerin | 15.00 wt % |
| Sorbitol | 10.00 wt % |
| Purified water | Balance wt % |

<1-2> Preparation of Lotion

Lotion was prepared by mixing the ingredients shown below following a method that is conventionally conducted in the art.

| *Lactococcus chungangensis* | 0.10 wt % |
|---|---|
| Glycerin | 3.00 wt % |
| Carbomer | 0.10 wt % |
| Xanthan gum | 0.05 wt % |
| 1,3-Butylene glycol | 3.00 wt % |
| Polyglyceryl-3 methyl glucose distearate | 1.50 wt % |
| Glyceryl stearate | 0.50 wt % |
| Cetylaryl alcohol | 0.30 wt % |
| Jojoba oil | 3.00 wt % |
| Liquid paraffin | 2.00 wt % |
| Squalane | 3.00 wt % |
| Dimethicone | 0.50 wt % |
| Tocopheryl acetate | 0.20 wt % |
| Triethanolamine | 0.10 wt % |
| Preservative, fragrant, colorant | trace |
| Purified water | Balance wt % |

Preparative Example 2

Preparation of Food Composition

<2-1> Preparation of Fermented Milk

Fermented milk was prepared using *Lactococcus chungangensis* of the present invention.

A culture broth (*Lactococcus chungangensis*: 1×10⁹ CFU/ml) was prepared by mixing crude milk (74.41%) and skimmed milk powder (6.45%) and adding culture seeds and *Lactococcus chungangensis*. For comparison, a culture liquid was prepared by adding only culture seeds to the same mixture composition. The sugar liquid was prepared, and mixed with each culture liquid prepared above, thereby manufacturing a fermented milk product.

<2-2> Preparation of Beverage

| | |
|---|---|
| Honey | 522 mg |
| Thioctic acid amide | 5 mg |
| Nicotinic acid amide | 10 mg |
| Sodium riboflavin hydrochloride | 3 mg |
| Pyridoxine hydrochloride | 2 mg |
| Inositol | 30 mg |
| Orthoic acid | 50 mg |
| *Lactococcus chungangensis*, and culture supernatant thereof | |
| Water | 200 ml |

A beverage was prepared using the above composition and contents by a conventional method.

<2-3> Preparation of Health Functional Food (Powder)

| | |
|---|---|
| *Lactococcus chungangensis* freeze-dried powder (1 × 10⁹ CFU/g) | 20 mg |
| Lactose | 100 mg |
| Talc | 10 mg |

A powder was prepared by mixing the above ingredients and then packaging the mixture in an airtight bag.

<2-4> Preparation of Health Functional Food (Tablet)

| | |
|---|---|
| *Lactococcus chungangensis* freeze-dried powder (1 × 10⁹ CFU/g) | 10 mg |
| Corn starch | 100 mg |
| Lactose | 100 mg |
| Magnesium stearate | 2 mg |

A tablet was prepared by mixing the above ingredients and then tableting the mixture according to an ordinary method for preparing a tablet preparation.

<2-5> Preparation of Health Functional Food (Capsule)

| | |
|---|---|
| *Lactococcus chungangensis* freeze-dried powder (1 × 10⁹ CFU/g) | 10 mg |
| Crystalline cellulose | 3 mg |
| Lactose | 14.8 mg |
| Magnesium stearate | 0.2 mg |

A capsule was prepared by mixing the above ingredients and then filling the mixture in a gelatin capsule according to an ordinary method for preparing a capsule preparation.

<2-6> Preparation of Health Functional Food (Mixed Powder) (1)

| | |
|---|---|
| *Lactococcus chungangensis* freeze-dried powder (1 × 10⁹ CFU/g) | 1 g |
| Vitamin mixture | Adequate quantity |
| vitamin A acetate | 70 μg |
| vitamin E | 1.0 mg |
| vitamin B1 | 0.13 mg |
| vitamin B2 | 0.15 mg |
| vitamin B6 | 0.5 mg |
| vitamin B12 | 0.2 μg |
| vitamin C | 10 mg |
| Biotin | 10 μg |
| Nicotinic acid amide | 1.7 mg |
| Folic acid | 50 μg |
| Calcium pantothenate | 0.5 mg |
| Mineral mixture | Adequate quantity |
| Ferrous sulfate | 1.75 mg |
| Zinc oxide | 0.82 mg |
| Magnesium carbonate | 25.3 mg |
| Potassium monophosphate | 15 mg |
| Dicalcium phosphate | 55 mg |
| Potassium citrate | 90 mg |
| Calcium carbonate | 100 mg |
| Magnesium chloride | 24.8 mg |

<2-7> Preparation of Health Functional Food (Mixed Powder) (2)

| | |
|---|---|
| *Lactococcus chungangensis* freeze-dried powder (1 × 10⁹ CFU/g) | 1 g |
| vitamin mixture | Adequate quantity |
| vitamin A | 700 μg |
| vitamin B1 | 1.2 mg |
| vitamin B2 | 1.4 mg |
| vitamin B6 | 1.5 mg |
| vitamin B12 | 2.4 μg |
| vitamin C | 100 mg |
| Niacin | 15 mg |
| Pantothenic acid | 5 mg |
| vitamin D | 5 μg |
| vitamin E | 11 mg |
| Biotin | 30 μg |
| Folic acid | 400 μg |
| Beta carotene | 500 μg |
| Mineral mixture | Adequate quantity |
| Zinc | 8.5 mg |
| Copper | 0.8 mg |
| Selenium | 55 μg |
| Chromium | 50 μg |
| Iodine | 150 μg |
| Mangnese | 3 mg |
| Molybdenum | 25 μg |

The composition ratios of the vitamin and the mineral mixtures were obtained by mixing relatively suitable ingredients for a health food in preferable examples, but the mixing ratio may be optionally varied. The above-described ingredients were mixed to prepare a granule by a conventional method for preparing a health food, and may be used for preparation of a health food composition according to a conventional method.

While the present invention has been described with reference to the particular illustrative embodiments, those skilled in the art to which the present invention pertains can understand that the present invention may be embodied in other specific forms without departing from the technical spirit or essential characteristics thereof. Therefore, the embodiments described above should be construed as as being exemplified and not limiting the present disclosure. The scope of the present invention is not defined by the detailed description as set forth above but by the accompanying claims of the invention, and it should also be understood that all changes or modifications derived from the definitions and scopes of the claims and their equivalents fall within the scope of the invention.

INDUSTRIAL APPLICABILITY

The composition comprising *Lactococcus chungangensis* as an active ingredient of the present invention has excellent effects of preventing or treating inflammatory diseases, inhibiting the release of major inflammation factors nitric oxide or prostaglandin E2, suppressing the release of major allergy-related factors β-hexosaminidase and histamine, and significantly inhibiting the production of skin disease-related cytokines and chemokines, and such efficacies have the same levels even when compared with a known skin disease medicine (Tacrolimus), while the composition of the present invention has antibacterial activity on *Staphylococcus aureus*, which is a microorganism causing secondary infection of atopic dermatitis, and thus is highly industrially applicable.

The invention claimed is:

1. A method for treating an inflammatory disease in a subject in need thereof, the method comprising administering to the subject *Lactococcus chungangensis* having an accession number of KCTC 12684BP in an amount effective to treat the inflammatory disease, wherein the inflammatory disease is any one selected from the group consisting of an inflammatory skin disease and an allergic disease.

2. The method of claim 1, wherein the allergic disease is any one selected from the group consisting of an allergic skin disease, atopic dermatitis, bronchial asthma, allergic rhinitis, allergic conjunctivitis, allergic otitis media, rash, asthma, and anaphylactic shock.

* * * * *

```
                          SEQUENCE LISTING

<160> NUMBER OF SEQ ID NOS: 14

<210> SEQ ID NO 1
<211> LENGTH: 21
<212> TYPE: DNA
<213> ORGANISM: Artificial Sequence
<220> FEATURE:
<223> OTHER INFORMATION: IL-4 sense

<400> SEQUENCE: 1
tcaaccccca gctagttgtc a                                              21

<210> SEQ ID NO 2
<211> LENGTH: 20
<212> TYPE: DNA
<213> ORGANISM: Artificial Sequence
<220> FEATURE:
<223> OTHER INFORMATION: IL-4 antisense

<400> SEQUENCE: 2
catcgaaaag cccgaaagag                                                20

<210> SEQ ID NO 3
<211> LENGTH: 23
<212> TYPE: DNA
<213> ORGANISM: Artificial Sequence
<220> FEATURE:
<223> OTHER INFORMATION: IL-5 sense

<400> SEQUENCE: 3
agcacagtgg tgaaagagac ctt                                            23

<210> SEQ ID NO 4
<211> LENGTH: 22
<212> TYPE: DNA
<213> ORGANISM: Artificial Sequence
<220> FEATURE:
<223> OTHER INFORMATION: IL-5 antisense

<400> SEQUENCE: 4
tccaatgcat agctggtgat tt                                             22

<210> SEQ ID NO 5
<211> LENGTH: 21
<212> TYPE: DNA
<213> ORGANISM: Artificial Sequence
<220> FEATURE:
<223> OTHER INFORMATION: IL-12 sense

<400> SEQUENCE: 5
gacacgcctg aagaagatga c                                              21

<210> SEQ ID NO 6
<211> LENGTH: 21
<212> TYPE: DNA
<213> ORGANISM: Artificial Sequence
<220> FEATURE:
<223> OTHER INFORMATION: IL-12 antisense

<400> SEQUENCE: 6
```
cgccattcca catgtcactg c                                               21

<210> SEQ ID NO 7
<211> LENGTH: 19
<212> TYPE: DNA
<213> ORGANISM: Artificial Sequence
<220> FEATURE:
<223> OTHER INFORMATION: IFN-gamma sense

<400> SEQUENCE: 7
aacgctacac actgcatct                                                  19

<210> SEQ ID NO 8
<211> LENGTH: 19
<212> TYPE: DNA
<213> ORGANISM: Artificial Sequence
<220> FEATURE:
<223> OTHER INFORMATION: IFN-gamma antisense

<400> SEQUENCE: 8
gagctcattg aatgcttgg                                                  19

<210> SEQ ID NO 9
<211> LENGTH: 19
<212> TYPE: DNA
<213> ORGANISM: Artificial Sequence
<220> FEATURE:
<223> OTHER INFORMATION: TNF-alpha sense

<400> SEQUENCE: 9
caggcggtgc ctatgtctc                                                  19

<210> SEQ ID NO 10
<211> LENGTH: 22
<212> TYPE: DNA
<213> ORGANISM: Artificial Sequence
<220> FEATURE:
<223> OTHER INFORMATION: TNF-alpha antisense

<400> SEQUENCE: 10
cgatcacccc gaagttcagt ag                                              22

<210> SEQ ID NO 11
<211> LENGTH: 23
<212> TYPE: DNA
<213> ORGANISM: Artificial Sequence
<220> FEATURE:
<223> OTHER INFORMATION: TARC sense

<400> SEQUENCE: 11
caggaagttg gtgagctggt ata                                             23

<210> SEQ ID NO 12
<211> LENGTH: 22
<212> TYPE: DNA
<213> ORGANISM: Artificial Sequence
<220> FEATURE:
<223> OTHER INFORMATION: TARC antisense

<400> SEQUENCE: 12
ttgtgttcgc ctgtagtgca ta                                              22

<210> SEQ ID NO 13
<211> LENGTH: 20
<212> TYPE: DNA

```
<213> ORGANISM: Artificial Sequence
<220> FEATURE:
<223> OTHER INFORMATION: GAPDH sense

<400> SEQUENCE: 13
aagctgtggc gtgatggccg                                           20

<210> SEQ ID NO 14
<211> LENGTH: 20
<212> TYPE: DNA
<213> ORGANISM: Artificial Sequence
<220> FEATURE:
<223> OTHER INFORMATION: GAPDH antisense

<400> SEQUENCE: 14
tgggccctca gatgcctgct                                           20
```